United States Patent
Scheiner

(10) Patent No.: US 11,400,293 B2
(45) Date of Patent: Aug. 2, 2022

(54) METHOD AND APPARATUS FOR STIMULATION

(71) Applicant: Medtronic, Inc., Minneapolis, MN (US)

(72) Inventor: Avram Scheiner, Vadnais Heights, MN (US)

(73) Assignee: MEDTRONIC, INC., Minneapolis, MN (US)

(*) Notice: Subject to any disclaimer, the term of this patent is extended or adjusted under 35 U.S.C. 154(b) by 0 days.

(21) Appl. No.: 16/811,954

(22) Filed: Mar. 6, 2020

(65) Prior Publication Data

US 2020/0281763 A1    Sep. 10, 2020

Related U.S. Application Data

(60) Provisional application No. 62/814,398, filed on Mar. 6, 2019.

(51) Int. Cl.
*A61N 1/36* (2006.01)
*A61F 5/56* (2006.01)
(Continued)

(52) U.S. Cl.
CPC .......... *A61N 1/3611* (2013.01); *A61B 5/0004* (2013.01); *A61B 5/0015* (2013.01);
(Continued)

(58) Field of Classification Search
CPC ............ A61N 1/36078; A61N 1/36139; A61N 1/4818; A61N 1/3611; A61N 1/025;
(Continued)

(56) References Cited

U.S. PATENT DOCUMENTS

| 4,989,617 A | 2/1991 | Memberg et al. |
| 6,044,297 A | 3/2000 | Sheldon et al. |

(Continued)

FOREIGN PATENT DOCUMENTS

| EP | 3355984 A1 | 8/2018 |
| EP | 3071288 B1 | 11/2018 |
| WO | 2011016864 A1 | 2/2011 |

OTHER PUBLICATIONS

International Search Report and Written Opinion dated May 28, 2020 in corresponding International Application No. PCT/US2020/021545.

(Continued)

*Primary Examiner* — Carl H Layno
*Assistant Examiner* — Anh-Khoa N Dinh
(74) *Attorney, Agent, or Firm* — Shumaker & Sieffert, P.A.

(57) ABSTRACT

A medical device system and method are disclosed for treating obstructive sleep apnea. The system includes a pulse generator and a medical electrical lead including multiple electrodes carried by a distal portion of an elongated lead body. The method includes advancing the distal portion within protrusor muscle tissue below the oral cavity and delivering electrical stimulation pulses via the electrodes to sustain a protruded state throughout a delivery time period to sustain a protruded state of a patient's tongue throughout the therapy delivery time period. The therapy delivery time period may span multiple respiration cycles.

20 Claims, 14 Drawing Sheets

(51) Int. Cl.
*A61N 1/372* (2006.01)
*A61N 1/02* (2006.01)
*A61B 5/00* (2006.01)
*A61B 5/024* (2006.01)
*A61B 5/11* (2006.01)
*A61B 7/02* (2006.01)
*A61B 5/389* (2021.01)

(52) U.S. Cl.
CPC .......... *A61B 5/0031* (2013.01); *A61B 5/4818* (2013.01); *A61B 5/7264* (2013.01); *A61F 5/566* (2013.01); *A61N 1/025* (2013.01); *A61N 1/3601* (2013.01); *A61N 1/36003* (2013.01); *A61N 1/36078* (2013.01); *A61N 1/36125* (2013.01); *A61N 1/36139* (2013.01); *A61N 1/37247* (2013.01); *A61N 1/37252* (2013.01); *A61B 5/024* (2013.01); *A61B 5/1116* (2013.01); *A61B 5/389* (2021.01); *A61B 7/023* (2013.01); *A61B 2562/0219* (2013.01); *A61N 1/36175* (2013.01)

(58) Field of Classification Search
CPC .............. A61N 1/3601; A61N 1/36125; A61N 1/37247; A61N 1/37252; A61F 5/566; A61B 5/0004; A61B 5/0015; A61B 5/0031; A61B 5/4818; A61B 5/7264; A61B 5/024; A61B 5/1116; A61B 2562/0219
See application file for complete search history.

(56) References Cited

U.S. PATENT DOCUMENTS

| | | | |
|---|---|---|---|
| 9,662,045 | B2 | 5/2017 | Skelton et al. |
| 9,757,560 | B2 | 9/2017 | Papay |
| 9,889,299 | B2 | 2/2018 | Ni et al. |
| 10,029,098 | B2 | 7/2018 | Papay |
| 10,065,038 | B2 | 9/2018 | Papay |
| 10,744,339 | B2 | 8/2020 | Makansi |
| 2008/0103407 | A1* | 5/2008 | Bolea ................ A61N 1/3606 600/529 |
| 2014/0228905 | A1* | 8/2014 | Bolea ................... A61F 5/56 607/42 |
| 2015/0224307 | A1 | 8/2015 | Bolea |
| 2017/0296815 | A1 | 10/2017 | Papay |
| 2020/0269044 | A1 | 8/2020 | Papay |
| 2020/0281763 | A1* | 9/2020 | Scheiner ............ A61B 5/4818 |
| 2020/0338358 | A1 | 10/2020 | Makansi |
| 2020/0346017 | A1 | 11/2020 | Caparso et al. |

OTHER PUBLICATIONS

International Preliminary Report on Patentability from International Application No. PCT/US2020/021545, dated Sep. 16, 2021, 8 pp.
Eastwood et al., "Bilateral Hypoglossal Nerve Stimulation for Treatment of Adult Obstructive Sleep Apnea," European Respiratory Journal, Jan. 9, 2020, 54 pp.

* cited by examiner

METHOD AND APPARATUS FOR STIMULATION

CROSS-REFERENCE TO RELATED APPLICATION

This application claims the benefit of and priority to U.S. Provisional Patent Application No. 62/814,398 filed Mar. 6, 2019, the entire disclosure of which is incorporated by reference herein.

TECHNICAL FIELD

This disclosure relates to a medical device system and method for therapeutic electrical stimulation for treatment of obstructive sleep apnea.

BACKGROUND

Implantable medical devices capable of delivering electrical stimulation pulses have been proposed or are available for treating a variety of medical conditions, such as cardiac arrhythmias and chronic pain as examples. Obstructive sleep apnea (OSA), which encompasses apnea and hypopnea, is a serious disorder in which breathing is irregularly and repeatedly stopped and started during sleep, resulting in disrupted sleep and reducing blood oxygen levels. OSA is caused by complete or partial collapse of the pharynx during sleep. In particular, muscles in a patient's throat intermittently relax thereby obstructing the upper airway while sleeping. Airflow into the upper airway can be obstructed by the tongue or soft pallet moving to the back of the throat and covering a smaller than normal airway. Loss of air flow also causes unusual inter-thoracic pressure as a person tries to breathe with a blocked airway. Lack of adequate levels of oxygen during sleep can contribute to abnormal heart rhythms, heart attack, heart failure, high blood pressure, stroke, memory problems and increased accidents. Additionally, loss of sleep occurs when a person is awakened during an apneic episode. Implantable medical devices capable of delivering electrical stimulation pulses have been proposed for treating OSA by electrically stimulating muscles around the upper airway that may block the airway during sleep.

SUMMARY

The techniques of this disclosure generally relate to an implantable medical device (IMD) system and methods for delivering OSA therapy. The IMD delivers electrical stimulation via electrodes deployed to a target stimulation region within the protrusor muscles of the tongue for activating the protrusor muscles to sustain a protruded state of the tongue throughout a therapy delivery period. The sustained protruded state of the tongue maintains an open upper airway throughout the delivery period, which may be sustained across multiple respiratory cycles, including both inhalation and exhalation phases. The electrodes are deployed, e.g., intramuscularly, to the target stimulation region of the protrusor muscles to avoid stimulation of nerves and muscles that may interfere with opening of the airway.

In one example, the disclosure provides an implantable medical device system including a medical electrical lead and a pulse generator. The medical electrical lead has an elongated lead body extending from a proximal lead end to a distal lead end with a distal portion proximate the distal lead end. Multiple electrodes are spaced apart along the distal portion of the lead body. The pulse generator is configured to receive the proximal lead end and includes a therapy delivery circuit configured to deliver electrical stimulation pulses via the electrodes to activate protrusor muscle tissue of a patient's tongue. The pulse generator includes a control circuit configured to control the therapy delivery circuit to continuously deliver the electrical stimulation pulses from a starting time of a therapy delivery time period to an ending time of the therapy delivery time period to sustain a protruded state of the patient's tongue throughout the therapy delivery time period, wherein the therapy delivery time period includes multiple respiration cycles including both inspiratory and expiratory phases.

In another example the disclosure provides a method performed by a medical device that includes continuously delivering electrical stimulation pulses from a starting time of a therapy delivery time period to an ending time of the therapy delivery time period by a therapy delivery circuit under the control of a control circuit of a medical device via electrodes carried by a distal portion of a first medical electrical lead coupled to the medical device. The electrical stimulation pulses activate protrusor muscle tissue of a patient's tongue to sustain a protruded state of the patient's tongue throughout the therapy delivery time period. The therapy delivery time period extends for multiple respiration cycles including inspiratory and expiratory phases.

In yet another example the disclosure provides a non-transitory computer readable medium storing instructions, which, when executed by a control circuit of a pulse generator, cause the pulse generator to continuously deliver electrical stimulation pulses from a starting time of a therapy delivery time period to an ending time of the therapy delivery time period via electrodes carried by a distal portion of a medical electrical lead coupled to the pulse generator. The electrical stimulation pulses activate protrusor muscle tissue of a patient's tongue to sustain a protruded state of the patient's tongue throughout the therapy delivery time period. The therapy delivery time period extends for multiple respiration cycles including inspiratory and expiratory phases.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

A medical device system for delivering electrical stimulation to the protrusor muscles of the tongue for the treatment of OSA is described herein. Electrical stimulation is delivered to cause the tongue of a patient to be a protruded state, during sleep, to avoid or reduce upper airway obstruction. As used herein, the term, "protruded state" with regard to the tongue refers to a position that is moved forward and/or downward compared to the non-stimulated position or a relaxed position. The protruded state is a state associated with the recruitment of protrusor muscles of the tongue (also sometimes referred to as "protruder" muscles of the tongue) including the genioglossus and geniohyoid muscles. A protruded state may be the opposite of a retracted and/or elevated position associated with the recruitment of the retractor muscles, e.g., styloglossus and hyoglossus muscles, which retract and elevate the tongue. Electrical stimulation is delivered to cause the tongue to move to and maintain a protruded state to prevent collapse, open or widen the upper airway of a patient to promote unrestricted or at least reduced restriction of airflow during breathing.

Figure 1:
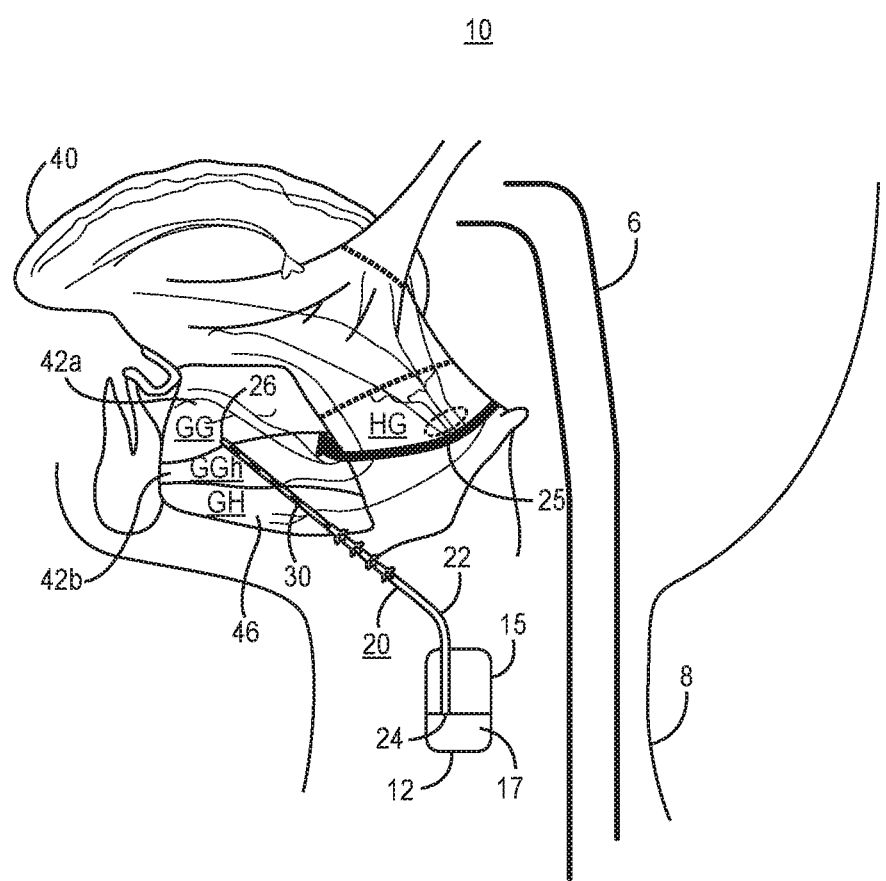
FIG. 1 is a conceptual diagram of an implantable medical device (IMD) system for delivering OSA therapy.

FIG. 1 is a conceptual diagram of an IMD system for delivering OSA therapy. The IMD system 10 includes an electrical medical lead 20 and a pulse generator 12. Pulse generator 12 includes a housing 15 enclosing circuitry of pulse generator 12, e.g., a control circuit, therapy delivery circuit, optional sensor, and telemetry circuit as described below in conjunction with FIG. 3. A connector assembly 17 is hermetically sealed to housing 15 and includes one or more connector bores for receiving at least one medical electrical lead used for delivering OSA therapy and, in some examples, for sensing electromyogram (EGM) signals.

Lead 20 includes a flexible, elongate lead body 22 that extends from a lead proximal end 24 to a lead distal end 26. At least two electrodes 30 are carried along a lead distal portion adjacent lead distal end 26 that are configured for insertion within the protrusor muscles 42a, 42b and 46 of the patient's tongue 40. The electrodes 30 are configured for implantation within soft tissue proximate the medial branches of the HGN that innervate the protrusor muscles of the tongue. The electrodes 30 may be referred to herein as "intramuscular electrodes," in contrast to an electrode that is placed on or along a nerve trunk or branch, such as a cuff electrode, used to directly stimulate the nerve trunk or branch. As such, lead 20 may be referred to herein as an "intramuscular lead" since the lead distal end and electrodes 30 are configured for advancement through the soft tissue, which may include the protrusor muscle tissue, to anchor electrodes 30 in proximity of the HGN branches that innervate the protrusor muscles 42a, 42b and 46. The term "intramuscular" with regard to electrodes 30 and lead 20 is not intended to be limiting, however, since the electrodes 30 may be implanted in connective tissue or other soft tissue proximate the medial HGN and its branches. Electrodes 30 carried by lead 20 are provided to stimulate the branches of the HGN that innervate the protrusor muscles 42a, 42b and 46 of the tongue 40 and/or motor points of the protrusor muscles.

The protrusor muscles are activated by electrical stimulation pulses generated by pulse generator 12 and delivered via the intramuscular electrodes 30 to move tongue 40 forward, to promote a reduction in obstruction or narrowing of the upper airway 6 during sleep. As used herein, the term "activated" with regard to the electrical stimulation of the protrusor muscles refers to electrical situation that causes depolarization or an action potential of the cells of the nerve innervating the protrusor muscles and motor points and subsequent depolarization and mechanical contraction of the protrusor muscle cells. In some cases, the muscles may be activated directly by the electrical stimulation pulses. The protrusor muscles that may be activated by stimulation via intramuscular electrodes 30 may include at least one or both of the right and/or left genioglossus muscle (GG) 42, which includes the oblique compartment (GGo) 42a and the horizontal compartment (GGh) 42b (referred to collectively as GG 42) and/or the right and/or left geniohyoid muscle (GH) 46. The GG muscle and GH muscle are innervated by a medial branch of the HGN (also referred to as the XIIth cranial nerve), while the hyoglossus and styloglossus muscles, which cause retraction and elevation of the tongue, are innervated by a lateral branch of the HGN.

The multiple distal electrodes 30 may be used to deliver bilateral or unilateral stimulation to the GG 42 and/or the GH 46 muscles via the medial branch of the HGN or branches thereof, also referred to herein as the "medial HGN." Distal electrodes 30 may be switchably coupled to output circuitry of pulse generator 12 to enable delivery of electrical stimulation pulses in a manner that selectively activates the right and left protrusor muscles in a cyclical or alternating pattern to avoid muscle fatigue while maintaining upper airway patency. Additionally or alternatively, electrical stimulation may be delivered to selectively activate the GG 42 and/or GH 46 muscles or portions thereof during unilateral stimulation of the left or right protrusor muscles.

The lead proximal end 24 includes a connector (not shown in FIG. 1) that is coupleable to connector assembly 17 of pulse generator 12 to provide electrical connection between circuitry enclosed by the housing 15 of pulse generator 12, e.g., including therapy delivery circuitry and control circuitry as described below in conjunction with FIG. 3. The lead body 22 encloses electrical conductors extending from each of the distal electrodes 30 to the proximal connector at proximal end 24 to provide electrical connection between output circuitry of pulse generator 12 and the electrodes 30.

Figure 2:
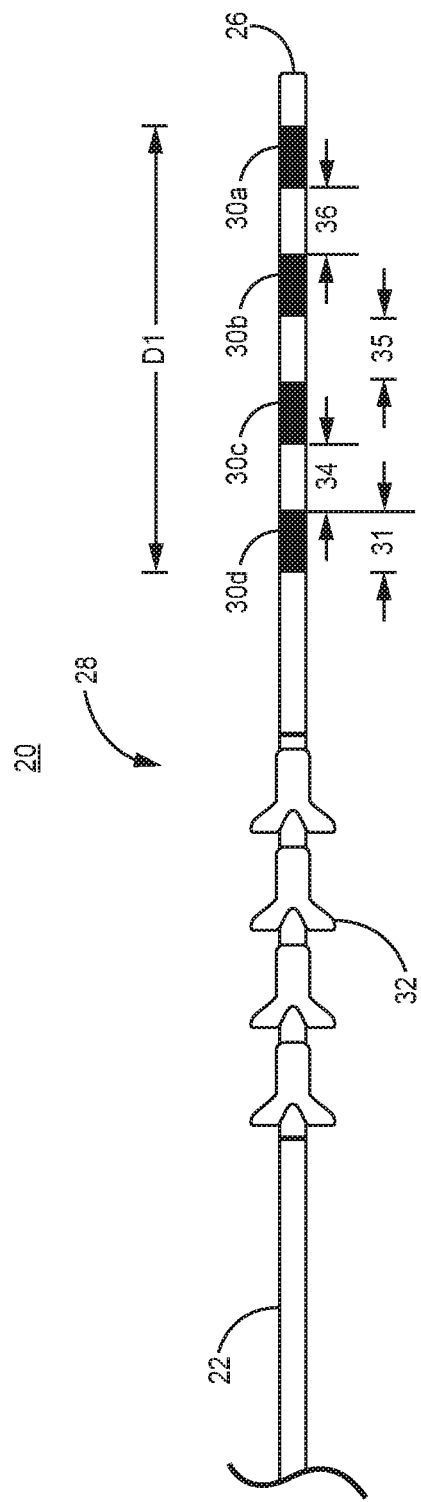
FIG. 2 is a conceptual diagram of a distal portion of a medical electrical lead included in the system of FIG. 1 according to one example.

FIG. 2 is a conceptual diagram of a distal portion 28 of intramuscular lead 20 according to one example. Lead 20 may include two or more electrodes, and in the example shown lead 20 includes four electrodes 30a, 30b, 30c, and 30d (collectively referred to as "electrodes 30") spaced apart longitudinally along lead body 22. Lead body 22 is a flexible lead body which may define one or more lumens within which insulated electrical conductors extend to a respective electrode 30a-30d. The distal most electrode 30a may be adjacent or proximate to lead distal end 26. Each of electrodes 30b, 30c and 30d are spaced proximally from the respective adjacent electrode 30a, 30b and 30c by a respective interelectrode distance 34, 35 and 36.

Each electrode 30a-30d is shown have equivalent electrode lengths 31. In other examples, however, electrodes 30a-30d may have electrode lengths 31 that are different from each other in order to optimize placement of the electrodes 30 or the resulting electrical field of stimulation relative to targeted stimulation sites corresponding to left and right portions of the HGN or branches thereof and/or motor points of the GG and GH muscles. The interelectrode spacings 34, 35 and 36 are shown to be approximately equal in FIG. 2, however in other examples the interelectrode spacings 34, 35 and 36 may be different from each other in order to optimize placement of electrodes 30 relative to the targeted stimulation sites. In some examples, electrodes 30a and 30b form an anode and cathode pair for delivering bipolar stimulation in one portion of the protrusor muscles, e.g., either the left or right GG and/or GH muscles or either a proximal or distal portion of the GG and/or GH muscles. Electrodes 30c and 30d may form a second anode and cathode pair for delivering bipolar stimulation in a different portion of the protrusor muscles (e.g., the other of the left or right portions or the other of the proximal or distal portions). Accordingly, the interelectrode spacing 35 between the two bipolar pairs 30a-30b and 30c-30d may be different than the interelectrode spacing 34 and 36 between the anode and cathode within each bipolar pair 30a-30b and 30c-30d.

In one example, the total distance D1 encompassed by electrodes 30a-30d along the distal portion 28d of lead body 22 may be about 20 millimeter, 25 millimeters, or 30 millimeters as examples. In one example, the total distance D1 is between 20 and 22 millimeters. The interelectrode spacings 34 and 36 within a proximal electrode pair 30c-30d and a distal electrode pair 30a-30b, respectively, may be 2 to 5 millimeters in some examples. The interelectrode spacing 35 separating the distal and proximal pairs 30a-30b and 30c-30d may be greater than the interelectrode spacings 34 and 36. For example, the interelectrode spacing 35 may be 4 to 6 millimeters in some examples. In one example, each of electrodes 30a-30d has an electrode length 31 of 3 mm, and each of interelectrode spacings 34, 35 and 36 is 3 mm.

In the example shown, each of electrodes 30a-30d is shown as a circumferential ring electrode which may be uniform in diameter with lead body 22. In other examples, electrodes 30 may include other types of electrodes such as a tip electrode, a helical electrode, a coil electrode, a segmented electrode, a button electrode as examples. For instance, the distal most electrode 30a may be provided as a tip electrode at the lead distal end 26 with the remaining three electrodes 30b, 30c and 30d being ring electrodes. When electrode 30a is positioned at the distal end 26, electrode 30a may be a helical electrode configured to screw into the muscle tissue at the implant site to additionally serve as a fixation member for anchoring the distal portion 28 of lead 20 at the targeted therapy delivery site. In other examples, one or more of electrodes 30a-d may be a hook electrode or barbed electrode to provide active fixation of the distal portion 28 of lead 20 at the therapy delivery site.

Lead 20 may include one or more fixation member 32 for minimizing the likelihood of lead migration. In the example shown, fixation member 32 includes multiple sets of tines which engage the surrounding tissue when lead distal portion 28 is positioned at the target therapy delivery site. The tines of fixation member 32 may extend radially and proximally at an angle relative to the longitudinal axis of lead body 22 to prevent or reduce retraction of lead body 22 in the proximal direction. Tines of fixation member 32 may be collapsible against lead body 22 when lead 20 is held within the confines of a lead delivery tool, e.g., a needle or introducer, used to deploy lead distal portion 28 at the target implant site. Upon removal of the lead delivery tool, the tines of fixation member 32 may spread to a normally extended position to engage with surrounding tissue and resist proximal and lateral migration of lead body 22. In other examples, fixation member 32 may include one or more hooks, barbs, helices, or other fixation mechanisms extending from one or more longitudinal locations along lead body 22 and/or lead distal end 26. Fixation member 32 may partially or wholly engage the GG, GH muscles and/or other muscles below the tongue, and/or other soft tissues of the neck, e.g., fat and connective tissue, when proximal end of lead body 20 is tunneled to an implant pocket of pulse generator 12. In other examples, fixation member 32 may include one or more fixation mechanisms located at other locations than the location shown in FIG. 2, including at or proximate to distal end 26, between electrodes 30, or otherwise more distally or more proximally than the location shown. The implant pocket of pulse generator 12 may be along the patient's neck 8 (see FIG. 1) Accordingly the length of the elongated lead body 22 from distal portion 28 to the lead proximal end 24 may be selected to extend from the a target therapy delivery site in the protrusor muscles to a location along the patient's neck where the pulse generator 12 is implanted. This length may be up to 10 cm or up to 20 cm as examples but may generally be 25 cm or less, though longer or shorter lead body lengths may be used depending on the anatomy and size of the individual patient.

Figure 3:
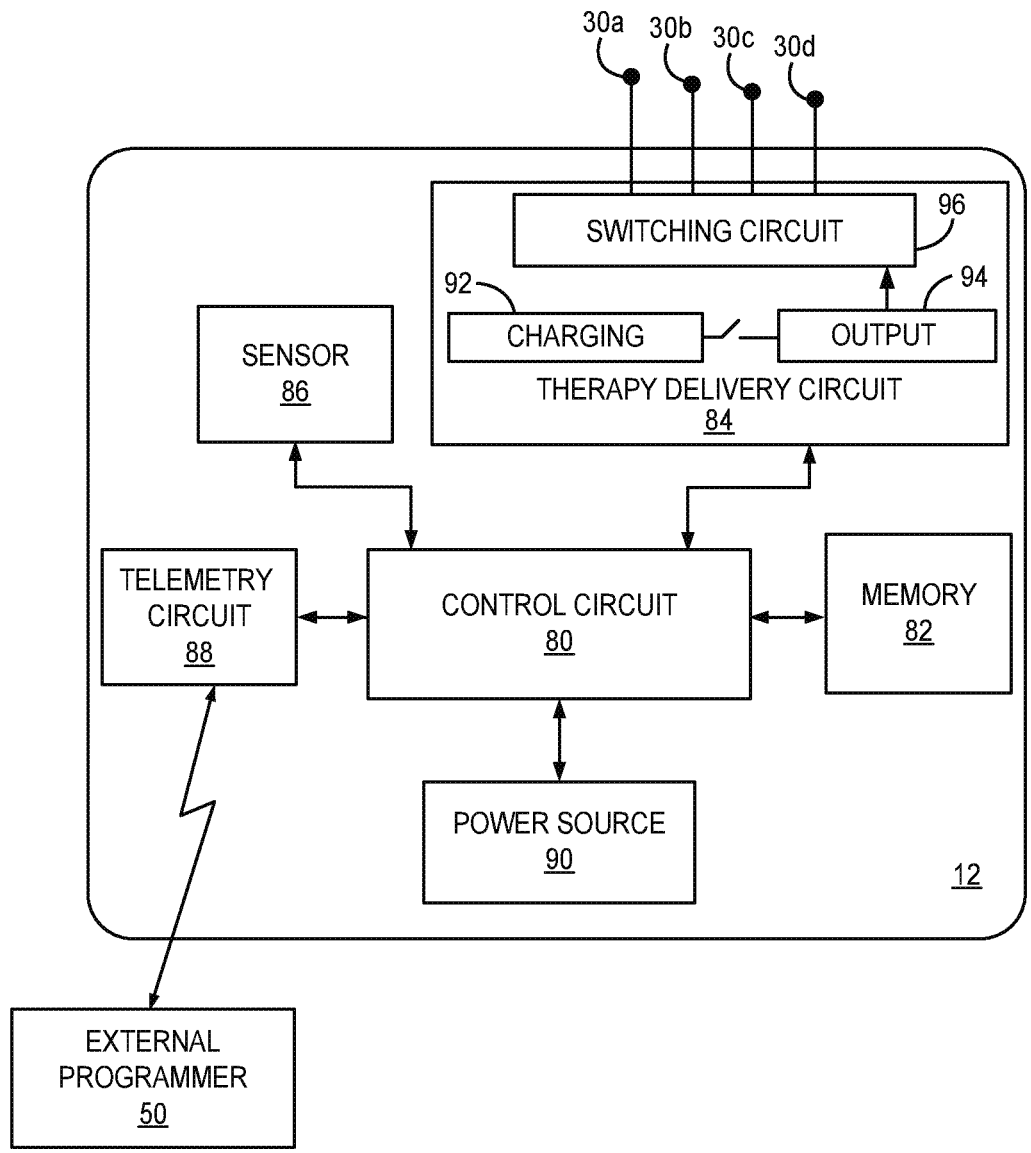
FIG. 3 is a conceptual diagram of a pulse generator included in the system of FIG. 1.

FIG. 3 is a conceptual diagram of pulse generator 12. Pulse generator 12 includes a control circuit 80, memory 82, therapy delivery circuit 84, an optional sensor 86, telemetry circuit 88 and power source 90. Power source 90 may include one or more rechargeable or non-rechargeable batteries for supplying electrical current to each of the control circuit 80, memory 82, therapy delivery circuit 84, sensor 86 and telemetry circuit 88. While power source 90 is shown in communication only with control circuit 80 for the sake of clarity, it is to be understood from the block diagram of FIG. 3 that power source 90 provides power as needed to each of the circuits and components of pulse generator 12 as needed. For example, power source 90 provides power to therapy delivery circuit 84 for generating electrical stimulation pulses.

The functional blocks shown in FIG. 3 represent functionality included in a pulse generator configured to delivery an OSA therapy and may include any discrete and/or integrated electronic circuit components that implement analog and/or digital circuits capable of producing the functions attributed to a pulse generator herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern cardiac medical device system, given the disclosure herein, is within the abilities of one of skill in the art.

Control circuit 80 communicates, e.g., via a data bus, with memory 82, therapy delivery circuit 84, telemetry circuit 88 and sensor 86 (when included) to control OSA therapy delivery and other pulse generator functions. As disclosed herein, control circuit 80 may pass control signals to therapy delivery circuit 84 to cause therapy delivery circuit 84 to deliver electrical stimulation pulses via electrodes 30 according to a therapy protocol that may include selective stimulation patterns of right and left portions of the GG and GH muscles and/or proximal and distal portions of the GG and GH muscles. Control circuit 80 may further be configured to pass therapy control signals to therapy delivery circuit 84 including stimulation pulse amplitude, stimulation pulse width, stimulation pulse number and frequency of a stimulation pulse train.

Memory 82 may store instructions for execution by a processor included in control circuit 80, stimulation control parameters, and other device-related or patient-related data. Control circuit 80 may retrieve therapy delivery control parameters and a therapy delivery protocol from memory 82 to enable control circuit 80 to pass control signals to therapy delivery circuit 84 for controlling the OSA therapy. Memory 82 may store historical data relating to therapy delivery for retrieval by a user via telemetry circuit 88. Therapy delivery data or information stored in memory 82 may include therapy control parameters used to deliver stimulation pulses as well as delivered therapy protocol(s), hours of therapy delivery or the like. When sensor 86 is included, patient related data determined from a sensor signal may be stored in memory 82 for retrieval by a user. In some examples, sensor 86 includes electrical signal sensing circuitry for sensing an electromyogram (EMG) signal using any combination of electrodes 30a-30d, which may be switchably coupled to sensor 86 to be used as EMG sensing electrodes when not used for stimulation. EMG signals may be used by control circuit 80 for detecting a sleep state and/or low tonal state of the protrusor muscles for use in controlling therapy delivery circuit 84 for delivering stimulation pulses to cause protrusion of the patient's tongue.

Therapy delivery circuit 84 may include a charging circuit 92, an output circuit 94, and a switching circuit 96. Charging circuit 92 may include one or more holding capacitors that are charged using a multiple of the battery voltage of power source 90, for example. The holding capacitors are switchably connected to output circuit 94, which may include one or more output capacitors that are coupled to a selected bipolar electrode pair via switching circuit 96. The holding capacitor(s) are charged to a programmed pacing pulse voltage amplitude by charging circuit 92 and discharged across the output capacitor for a programmed pulse width. Charging circuit 92 may include capacitor charge pumps or an amplifier for the charge source to enable rapid recharging of holding capacitors included in charging circuit 92. Therapy delivery circuit 84 responds to control signals from control circuit 80 for generating a delivering trains of pulses to produce sustained tetanic contraction of the GG and/or GH muscles or portions thereof to move the tongue forward and avoid upper airway obstruction.

Output circuit 94 may be selectively coupled to bipolar pairs of electrodes 30a-30d via switching circuit 96. Switching circuit 96 may include one or more switches activated by timing signals received from control circuit 80. Electrodes 30a-30d may be selectively coupled to output circuit 94 in a time-varying manner to deliver stimulation to different portions of the protrusor muscles at different time to avoid fatigue, without requiring stimulation to be withheld completely. In contrast to OSA therapy systems that rely on a sensor for sensing the inspiratory phase of respiration to coordinate the therapy with the inspiratory phase, the intramuscular electrodes 30 positioned to stimulate different portions of the protrusor muscles does not require synchronization to the respiratory cycle. Alternation of stimulation locations within the protrusor muscles allows different portions of the muscles to rest while other portions are activated to avoid collapse of the tongue against the upper airway while also avoiding muscle fatigue. Switching circuit 96 may include a switch array, switch matrix, multiplexer, or any other type of switching device(s) suitable to selectively couple therapy delivery circuit 84 to bipolar electrode pairs selected from electrodes 30. Bipolar electrode pairs may be selected one at a time or may be selected two or more at time to allow overlapping stimulation of two or more different portions of the protrusor muscles. Overlapping stimulation times of two portions of the protrusor muscles, for example left and right or proximal and distal may maintain a forward position of the tongue and allow a ramping up and ramping down of the electrical stimulation being delivered to two different portions of the protrusor muscles.

Sensor 86 is optional and may include one or more sensors for monitoring a patient condition. For example, sensor 86 may include a patient posture sensor for detecting when the patient is in a reclined position and likely to need OSA therapy. Control circuit 80 may monitor the patient posture sensor signal received from sensor 86 for determining when to start OSA therapy. The posture sensor may be implemented as a multi-axis accelerometer. The DC component of the signal produced by each accelerometer axis corresponds to gravitational force exerted along that axis or vector. As such, the DC component of each axis may be used for determining the patient's posture. A posture sensor that may be used in pulse generator 12 is generally disclosed in U.S. Pat. No. 6,044,297 (Sheldon, et al.), incorporated herein by reference in its entirety. In some examples, sensor 86 may include a patient activity sensor, such as an accelerometer or other motion sensor, that produces a signal correlated to patient physical activity or other motion, such as vibrations in the patient's airways associated with sleep apnea. Control circuit 80 may determine that the patient is asleep based on the patient posture, time of day, patient physical activity or any combination thereof. Therapy delivery circuit 84 may respond to a sleep detection signal from control circuit 80 by initiating the OSA therapy delivery.

As indicated above, sensor 86 may be configured for sensing EMG signals using electrodes 30a-30d (when a stimulation pulse is not being delivered by an electrode used for sensing). In other examples, dedicated EMG sensing electrodes may be carried by housing 15 and/or lead body 22 and coupled to sensor 86 for EMG signal monitoring. EMG signal monitoring by control circuit 80 may allow detection of a low tonal state of the GG and/or GH muscles indicating a susceptibility to upper airway collapse. Detection of low tonal state of the protrusor muscles may be a trigger for delivering OSA therapy. In other instances, EMG monitoring may be used alone or in conjunction with other sensor signals for detecting a sleep state for use in triggering the delivery of OSA therapy. EMG monitoring may further be used in monitoring for fatigue of the stimulated GG and/or GH muscles and may be used in a closed loop manner by control circuit 80 to control the duty cycle of electrical stimulation pulse trains delivered by therapy delivery circuit 84 to minimize or avoid fatigue and/or allow adequate fatigue recovery time between duty cycle on times.

In other examples, sensor 86 may include a motion sensor, an acoustical sensor or a microphone for detecting vibration or sounds in the upper airway and be indicative of OSA. Control circuit 80 may detect an onset of OSA and trigger therapy delivery circuit 84 to respond by initiation electrical stimulation therapy of the protrusor muscles. A motion sensor may produce a motion signal that is correlated to the movement of the patient's tongue into and out of a protruded state and may be used to detect adequate protrusion and/or fatigue of the stimulated muscle for use in controlling the duty cycle, pulse amplitude and/or stimulating electrode vector of the electrical stimulation therapy delivered by therapy delivery circuit 84. Sensor 96 may be configured to produce a signal that is correlated to protrusor muscle tonal state for use by control circuit 80 for detecting a low tonal state predictive of upper airway obstruction, detecting protrusor muscle fatigue, and/or detecting a protruded state of tongue 40. Therapy delivery circuit 84 may be configured to respond to a detection of the protrusor muscle tonal state by control circuit 80 by adjusting one or more control parameters used to control stimulation pulse delivery.

However, sensor 86 is optional. In some examples, the patient may initiate OSA therapy manually using a patient programmer at the time the patient is ready to go to sleep. In other examples, OSA therapy may be started and stopped at scheduled times of day. Control circuit 80 may include a clock for scheduling the time that OSA therapy is started and stopped by therapy delivery circuit 84. Since synchrony of the electrical stimulation of the protrusor muscles with inspiration is not required, a sensor for detecting respiration phase may be omitted.

Telemetry circuit 88 is optional but may be included to enable bidirectional communication with an external programmer 50. A user, such as the patient 8, may manually adjust therapy control parameter settings, e.g., as described in Medtronic's Patient Programmer Model 37642, incorporated by reference in its entirety. The patient may make limited programming changes such as small changes in stimulation pulse amplitude and pulse width. The patient may turn the therapy on and off or to set timers to turn the therapy on or off using external programmer 50 in wireless telemetric communication with telemetry circuit 88.

In other examples, a user, such as a clinician, may interacts with a user interface of an external programmer 50 to program pulse generator 12 according to a desired OSA therapy protocol. For example, a Physician Programmer Model 8840 available from Medtronic, Inc., Minneapolis, Minn., may be used by the physician to program pulse generator 12 for delivering electrical stimulation.

Programming of pulse generator 12 may refer generally to the generation and transfer of commands, programs, or other information to control the operation of pulse generator 12. For example, external programmer 50 may transmit programs, parameter adjustments, program selections, group selections, or other information to control the operation of pulse generator 12, e.g., by wireless telemetry. As one example, external programmer 50 may transmit parameter adjustments to support therapy changes. As another example, a user may select programs or program groups. A program may be characterized by an electrode combination, electrode polarities, voltage or current amplitude, pulse width, pulse rate, therapy duration, and/or pattern of electrode selection for delivering patterns of alternating portions of the protrusor muscles that are being stimulated. A group may be characterized by multiple programs that are delivered simultaneously or on an interleaved or rotating basis. These programs may adjust output parameters or turn the therapy on or off at different time intervals.

In some cases, external programmer 50 may be characterized as a physician or clinician programmer if it is primarily intended for use by a physician or clinician. In other cases, external programmer 50 may be characterized as a patient programmer if it is primarily intended for use by a patient. A patient programmer 50 is generally accessible to patient 12 and, in many cases, may be a portable device that may accompany the patient throughout the patient's daily routine. In general, a physician or clinician programmer may support selection and generation of programs by a clinician for use by pulse generator 12, whereas a patient programmer may support adjustment and selection of such programs by a patient during ordinary use.

External programmer 50 may present patient related and/or device related data retrieved from memory 82 via telemetry circuit 88. For example patient posture data stored in memory 82 from the detected posture states of patient 8 when sensor 86 is included may be presented on a display of external programmer 50, e.g., as generally described in U.S. Pat. No. 9,662,045 (Skelton, et al.), incorporated by reference in its entirety. Additionally or alternatively external programmer 50 may present sleep sound or motion data stored in memory 82 as determined from signals from sensor 86. Additionally or alternatively, the time periods in which the patient is lying down can be acquired based on patient posture detection using sensor 86 and a history of such data can be stored into memory 82 and retrieved and displayed by external programmer 50.

Figure 4:
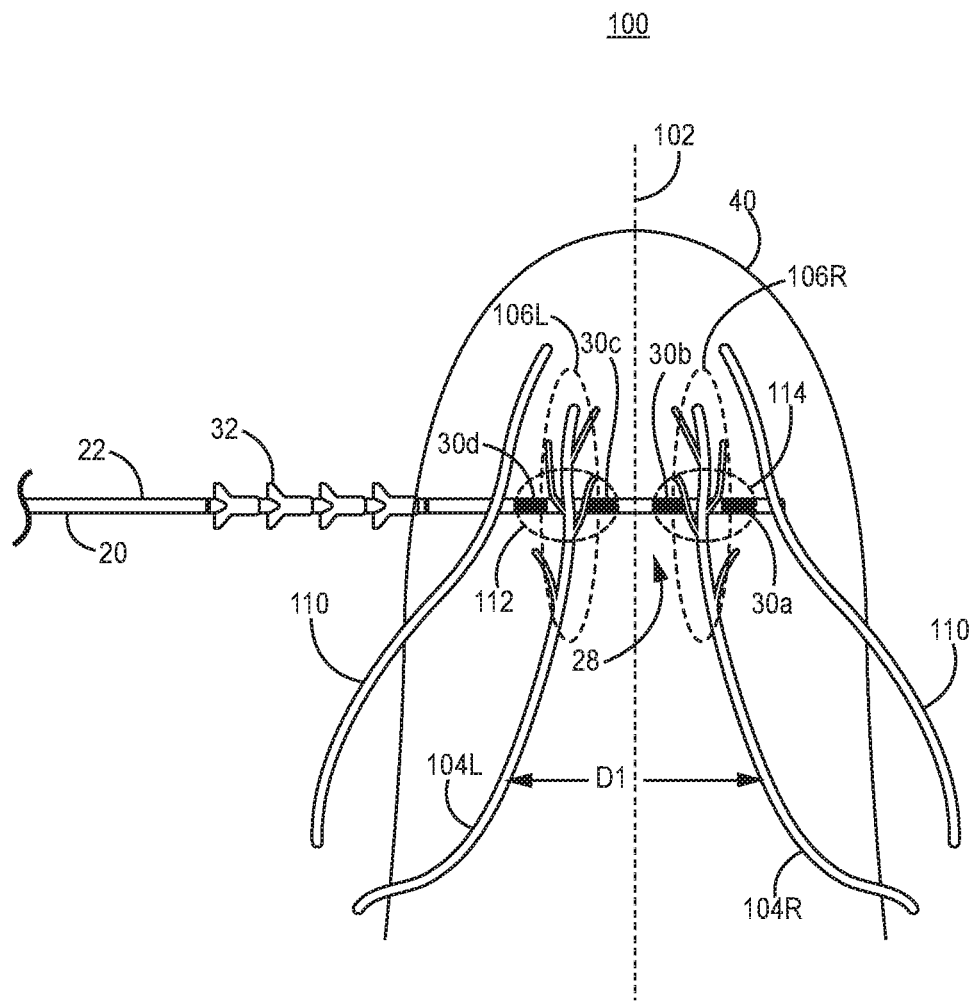
FIG. 4 is a conceptual diagram of the placement of the distal portion of the lead FIG. 2 for delivering OSA therapy according to one example.

FIG. 4 is a conceptual diagram of the placement of the distal portion of lead 20 for delivering OSA therapy according to one example. The left medial HGN 104L and right medial HGN 104R innervate the GG and GH muscles (see FIG. 1) which pull the tongue 40 forward and down. The targeted therapy delivery regions 106L and 106R of the left and right medial HGN 104L and 104R, respectively, and/or their branches innervating the GG and GH muscles are indicated by dashed line. The targeted therapy delivery regions 106L and 106R are generally parallel to the midline 102 of tongue 40 and anterior to the root of the tongue. Compared to the relatively more proximal placement of a nerve cuff electrode along the HGN, the distal portion 28 of lead 20 can be advanced further anteriorly or distally along and/or near the HGN to promote exclusive recruitment of the protrusor muscles with a low likelihood or complete avoidance of recruiting the retrusor muscles.

In some examples, the distal portion 28 of lead 20 is advanced approximately perpendicular to midline 102, inferior to the lingual branches of the trigeminal nerves 110 and inferior to both of the left and right medial HGN 104L and 104R to traverse both regions 106L and 106R and minimize the likelihood of unwanted recruitment of other nerves and retrusor muscles. In this way, electrodes 30 are placed a distance inferiorly from the lingual branches of the trigeminal nerves 110 so as not to activate sensory nerves of the tongue. The electrodes are placed anteriorly, for example within or along the GG muscle or at least anterior to the hyoglossus muscle and sternoglossus muscle to avoid activation of the hyoglossus and sternoglossus muscles which act to retract and/or elevate the tongue and may counteract the effectiveness of the OSA therapy.

In order to position the most distal two electrodes 30a and 30b in or along the target region 106R and the most proximal two electrodes 30c and 30d in or along the target region 106 L (or vice versa if the surgical approach is from the right instead of the left side of tongue 40 as shown), the total distance D1 encompassed by electrodes 30a-30d along distal portion 28 may be limited to a maximum of 30 millimeters or 25 millimeters as examples. Distal end 26 of lead 20 may be inserted from an inferior approach from under the mandible or from a superior approach from the floor of the oral cavity to advance the distal portion across the midline 102, approximately perpendicular to midline 102. Electrode placement may be verified using fluoroscopy or other imaging techniques and through testing of stimulation pulse delivery to verify an observed protrusion response to the stimulation.

In this example, electrical stimulation pulses delivered by distal bipolar electrode pair 30a and 30d produce an electrical field 114 (shown conceptually) in the target region 106R that captures the right HGN 104R and/or branches thereof for causing contraction of the right GG and/or GH muscles to cause protrusion of tongue 40. Electrical stimulation pulses delivered by proximal bipolar electrode pair 30c and 30d produce an electrical field 112 (shown conceptually) in the target region 106L that captures the left HGN 104L and/or branches thereof for causing contraction of the left GG and/or GH muscles to cause protrusion of tongue 40.

In some examples, depending on electrode spacing and relative placement to the right and left HGNs 104R and 104L, the inner electrodes 30b and 30c may be used as a bipolar pair for delivering electrical stimulation pulses that produce an electrical field (not illustrated) that encompasses at least a portion of the target regions 106L and/or 106R. In still other examples, the outer electrodes 30a and 30d may be used as a bipolar pair for delivering electrical stimulation pulses that produce an electrical field (not illustrated) that encompasses at least a portion of the target regions 106L and/or 106R. Switching circuit 96 may be configured to select bipolar pairs from any combination of the available electrodes 30, e.g., 30a and 30b, 30a and 30c, 30a and 30d, 30b and 30c, 30b and 30d or 30c and 30d. Time varying electrical fields produced by sequentially selecting different electrode pairs may allow different branches of the medial HGN to be stimulated, thereby recruiting different portions of the protrusor muscles during a sequential stimulation protocol, promoting sustained protrusion of the tongue 40 while avoiding or reducing fatigue. Fatigue is reduced compared to stimulation using a single electrical field produced by stimulation from one electrode pair, such as a nerve cuff electrode. Fatigue may be reduced by sequentially selecting electrode pairs during continuous stimulation pulse delivery over an extended therapy delivery period compared to using a single electrode pair, even when stimulation delivered using the single electrode pair is intermittent and synchronized to the inspiratory phase of respiration allowing rest during the expiratory phase of respiration.

Switching circuit may further select the polarity (anode or cathode) of each electrode within a selected bipolar pair. Bipolar pairs are sequentially selected during electrical stimulation delivery to produce different electrical fields encompassing different portions of the targeted regions 106L and 106R. Sequential selection of bipolar pairs may occur in an overlapping or non-overlapping manner. By sequentially selecting different bipolar pairs during stimulation delivery different portions of the HGN 104L and HGN 104R or branches thereof may be captured at different times, resulting in recruitment of different portions of the left and/or right GG and/or GH muscles for causing and maintaining protrusion of tongue 40.

As described below, the electrical stimulation pulses are delivered to sequentially selected electrode pairs to cause sustained protrusion of tongue 40 over a time period that encompasses multiple respiratory cycles. The respiratory cycles are consecutive in some examples and include both the expiration and inspiration phases of the consecutive respiratory cycles. Continuous electrical stimulation delivery via sequentially selected electrode pairs over an extended time period during sleep maintains the tongue 40 in a protruded state to avoid or reduce airway obstruction. By sequentially selecting two or more bipolar pairs selected from electrodes 30a-30d to deliver the electrical stimulation pulses to different portions of the protrusor muscles during the extended time period fatigue of the protrusor muscles is reduced or avoided. Since the electrical stimulation is delivered to cause continuous or sustained protrusion of tongue 40, the electrical stimulation pulses are delivered independent of the patient's respiration cycle, e.g., without being synchronized to or timed relative to the inspiratory or expiratory phases of respiration. The extended time period over which the electrical stimulation is delivered to cause continuous protrusion of the tongue 40 may be several minutes up to several hours and may extend a majority of the time that the patient is asleep, e.g., up to eight hours or more.

Figure 5:
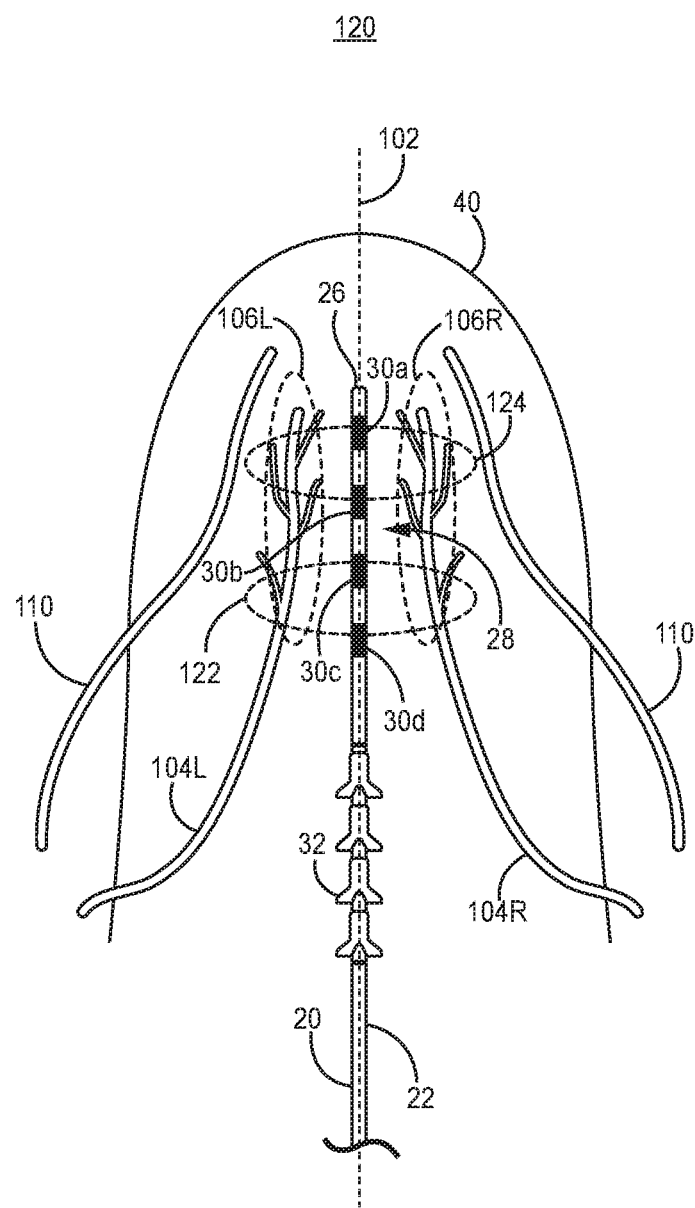
FIG. 5 is a conceptual diagram of the distal portion of lead the lead of FIG. 2 deployed for delivering OSA therapy according to another example.

FIG. 5 is a conceptual diagram 120 of the distal portion 28 of lead 20 deployed for delivering OSA therapy according to another example. In this example, distal portion 28 carrying electrodes 30 is advanced approximately along or parallel to midline 102 of tongue 40. In the example shown, lead body 22 is shown approximately centered along midline 102, however in other examples lead body 22 may be laterally offset from midline 102 in the left or right directions but is generally medial to both of the left HGN 104L and the right HGN 104R. The distal end 26 of lead 20 may be inserted inferiorly to the body of tongue 40, e.g., at a percutaneous insertion point along the submandibular triangle, in the musculature below the floor of the oral cavity. The distal end 26 is advanced to position electrodes 30 medially to the left and right HGNs 104L and 104R, e.g., approximately midway between the hyoid bone the mental protuberance (chin). An electrical field produced by stimulation pulses delivered between any bipolar pair of electrodes selected from electrodes 30 may encompass a portion of both the left target region 106L and the right target region 106R to produce bilateral stimulation of the HGNs 104L and 104R and therefore bilateral recruitment of the protrusor muscles. Bilateral recruitment of the protrusor muscles may provide greater airway opening than unilateral stimulation that is generally performed using a nerve cuff electrode along the HGN. For example, electrical stimulation pulses delivered using electrodes 30a and 30b may produce electrical field 122 (shown conceptually) encompassing a portion of both of the left and right target regions 106L and 106R. Electrical stimulation pulses delivered using electrodes 30c and 30d may produce electrical field 124 (shown conceptually) encompassing a portion of both of the left and right target regions 106L and 106R. The portions of the left and right target regions 106L and 106R encompassed by electrical field 122 are posterior portions relative the portions of the left and right target regions 106L and 106R encompassed by electrical field 124.

In some examples, electrical stimulation is delivered by pulse generator 12 by sequentially selecting different electrode pairs from among the available electrodes 30 to sequentially recruit different bilateral anterior and bilateral posterior portions of the HGNs 104L and 104R. This electrode selection may result in recruitment of different anterior and posterior portions of the protrusor muscles. The sequential selection of different electrode pairs may be overlapping or non-overlapping. The electrical stimulation is delivered throughout an extended time period encompassing multiple respiratory cycles independent of the timing of respiratory cycles to maintain a protruded state of tongue 40 from the beginning of the time period to the end of the time period. The electrodes 30 may be selected in bipolar pairs comprising the most distal pair 30a and 30b, the outermost pair 30a and 30d, the innermost pair 30b and 30c, the most proximal pair 30c and 30d or alternating electrodes along lead body 22, e.g., 30a and 30c or 30b and 30d. Sequential selection of two or more different electrode pairs allows for sequential recruitment of different portions of the protrusor muscles to reduce the likelihood of fatigue.

In some examples, electrical stimulation delivered using an electrode pair, e.g., 30a and 30b, that is relatively more distal along distal lead portion 28 and implanted relatively anteriorly along tongue 40 may recruit a greater portion of anterior muscle fibers, e.g., within the GG muscle. Electrical stimulation delivered using an electrode pair, e.g., 30c and 30d, that is relatively more proximal along distal lead portion 28 and implanted relatively posteriorly along tongue 40 may recruit a greater portion of posterior muscle fibers, e.g., within the GH muscle. Sequential selection of electrodes 30 for delivering electrical stimulation pulses allows sequential recruitment in overlapping or non-overlapping patterns of anterior and posterior portions of the protrusor muscles to sustain the tongue in a protruded state throughout the extended time period while reducing or avoiding muscle fatigue.

Figure 6:
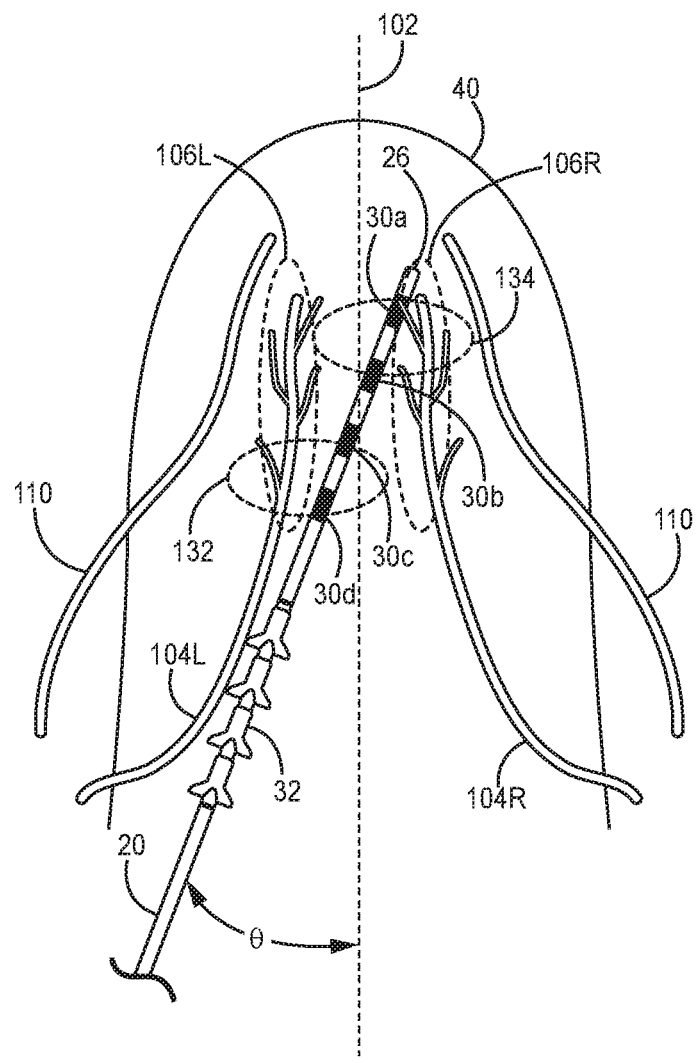
FIG. 6 is a conceptual diagram of the deployment of the distal portion of the lead of FIG. 2 for delivery of OSA therapy according to another example.

FIG. 6 is a conceptual diagram of the deployment of the distal portion 28 of lead 20 for delivery of OSA therapy according to another example. In this example, distal portion 28 carrying electrodes 30 is advanced at an oblique angle across midline 102 of tongue 40. In the example shown, distal portion 28 of lead body 22 is advanced obliquely across midline 102 such that one pair of electrodes, distal most electrodes 30a and 30b, is positioned along the right side of midline 102 for electrical stimulation delivery in the right target region 106R. The other pair of electrodes, proximal most electrodes 30c and 30d, is positioned along the left side of midline 102 for electrical stimulation delivery in target region 106 L. The oblique angle θ, at which distal portion 28 crosses midline 102, may be between 20 degrees and 70 degrees, as examples with no limitation intended. Distal portion 28 of lead 20 may extend at any angle between the perpendicular position shown in FIG. 4 and the parallel position shown in FIG. 5.

The distal end 26 of lead 20 may be inserted inferiorly to the mandible, e.g., at a percutaneous insertion point along the submandibular triangle, which may be a lateral point along the left or right medial side of the mandible. The distal end 26 may be advanced obliquely toward and across midline 102 to position electrodes 30 along both sides of the midline 102 and proximate both of the left and right HGNs 104L and 104R. Stimulation test pulses may be delivered to assist in determination of the final placement of the distal portion 28 of lead 20, e.g., resulting in independent recruitment of each of the left and right GG and/or GH muscles.

An electrical field 134 produced by stimulation pulses delivered between the distal most bipolar pair of electrodes selected from electrodes 30, e.g., 30a and 30b, may encompass a portion of the right target region 106R. Electrical stimulation pulses delivered using electrodes the most proximal electrodes, e.g., electrodes 30c and 30d, may produce electrical field 132 encompassing at least a portion of the left target region 106L. In some instances, depending on placement of the electrodes and magnitude of the stimulation energy being delivered, the electrical fields 132 and 134 may encompass portions of both the right and left target regions 106R and 106L, enabling bilateral recruitment of protrusor muscles using either the distal electrode pair 30a-30b or the proximal electrode pair 30c-30d. The portion of the left target region 106L encompassed by electrical field 132 may be relatively posterior to the portion of the right target region 106R encompassed by electrical field 134. When the outermost electrodes 30a and 30d or other electrodes having a relatively greater interelectrode distance, e.g., 30a and 30c or 30b and 30d, are selected as a bipolar pair, stimulation of both left and right HGNs 104L and 104R may be achieved, resulting in bilateral recruitment. When electrodes having a relatively smaller interelectrode distance are selected in a bipolar pair, e.g., electrodes 30a and 30b, 30b and 30c, or 30c and 30d, recruitment of relatively more anterior, relatively more posterior, relatively more left or relatively more right portions of the protrusor muscles may be achieved, depending on the oblique angle θ, electrode spacing, and electrode placement relative to the medial HGNs 104L and 104R and branches thereof.

In some examples, electrical stimulation is delivered by pulse generator 12 by repeatedly selecting two or more different electrode pairs in sequence from among the available electrodes 30 to sequentially recruit different left, right, anterior, posterior, bilateral, bilateral anterior and/or bilateral posterior portions of the protrusor muscles. The sequential selection of different electrode pairs may be overlapping or non-overlapping. The electrical stimulation is delivered throughout an extended time period encompassing multiple respiratory cycles independent of the timing of respiratory cycles, in particular independent of the timing of inspiration or expiration, to maintain a protruded state of tongue 40 from the beginning of the time period to the end of the time period. Sequential recruitment of different portions of the protrusor muscles may reduce the likelihood of fatigue while sustaining a protruded state of tongue 40.

Figure 7:
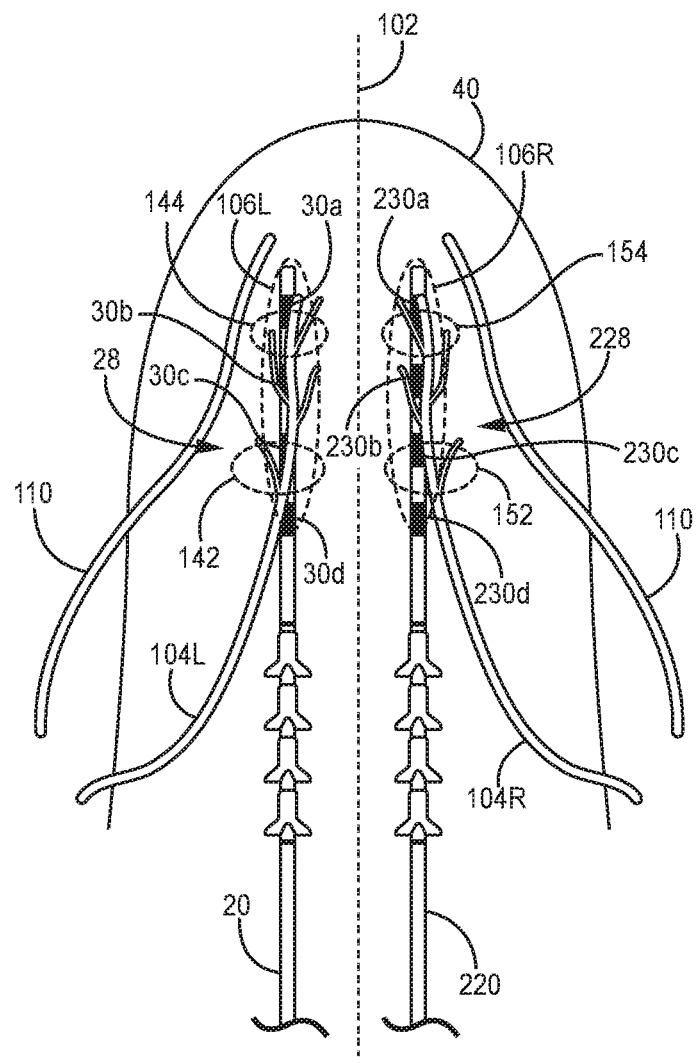
FIG. 7 is a conceptual diagram of the distal portion of a dual lead system for delivering OSA therapy.

FIG. 7 is a conceptual diagram of the distal portion of a dual lead system for delivering OSA therapy. In this example, one lead 20 is advanced anteriorly approximately parallel to midline 102 and offset, e.g. by 5-8 millimeters to the left of midline 102, to position distal portion 28 and electrodes 30 in or adjacent to the left target region 106L. A second lead 220 is advanced anteriorly approximately parallel to midline 102 but offset laterally to the right of midline 102 to position distal portion 228 and electrodes 230 in or adjacent the right target region 106R. Lead 20 may be inserted from a left lateral or posterior approach of the body of tongue 40, and lead 230 may be inserted from a right lateral or posterior approach of the body of tongue 40. In other examples, both leads 20 and 220 may be inserted from only a left or only a right approach with one lead traversing midline 102 to position the electrodes 30 or 230 along the opposite side of midline 102 from the approaching side. Lead 20 and/or lead 220 may be advanced at an oblique angle relative to midline 102 but may not cross midline 102. In other examples, one or both leads 20 and 220 may approach and cross midline 102 at an oblique angle such that one or both of distal portions 28 and 228 extend in or adjacent to both the right and left target regions 106L and 106R, similar to the orientation shown in FIG. 6.

In the example shown, relatively more localized control of the recruitment of left, right, anterior and posterior portions of the protrusor muscles may be achieve by selecting different electrode pairs from among the electrodes 30a through 30d and 230a through 230d. For example, any combination of electrodes 30a through 30d may be selected for delivering electrical stimulation pulses to the left portions of the protrusor muscles. More distal electrodes 30*a* and 30*b* may be selected for stimulation of more anterior portions of the left protrusor muscles (corresponding to electrical field 144) and more proximal electrodes 30*c* and 30*d* may be selected for stimulation of more posterior portions of the left protrusor muscles (corresponding to electrical field 142). Any combination of electrodes 230*a* through 230*d* may be selected for delivering electrical stimulation pulses to the right portions of the protrusor muscles. More distal electrodes 230*a* and 230*b* may be selected for stimulation of more anterior portions of the right protrusor muscles (corresponding to electrical field 154) and more proximal electrodes 230*c* and 230*d* may be selected for stimulation of more posterior portions of the right protrusor muscles (corresponding to electrical field 152).

Switching circuit 96 may be configured to select electrode pairs that include one electrode on one of leads 20 or 220 and another electrode on the other lead 20 or 220 to produce an electrical field (not shown) that encompasses portions of both the left target region 106L and the right target region 106R simultaneously for bilateral stimulation. Any combination of the available electrodes 30*a* through 30*d* and electrodes 230*a* through 230*d* may be selected as two or more bipolar pairs, which are selected in a repeated, sequential pattern to sequentially recruit different portions of the two target regions 106L and 106R. The sequential selection of electrode pairs may be overlapping or non-overlapping, but electrical stimulation pulses are delivered without interruption at one or more selected frequencies throughout an extended time period to maintain tongue 40 in a protruded state from the beginning of the time period to the end of the time period, encompassing multiple respiratory cycles.

In the example of FIG. 7 including two leads, two pairs of electrodes may be selected simultaneously and sequentially with one or more other pairs of electrodes. For example, electrodes 30*a* and 30*b* may be selected as one bipolar pair and electrodes 230*c* and 230*d* may be selected as a second bipolar pair for simultaneous stimulation of the left, anterior portion of the target region 106L and the right posterior portion of the target region 106R. The electrodes 30*c* and 30*d* may be selected as the next bipolar pair from lead 20, simultaneously with electrodes 230*a* and 230*b* selected as the next bipolar pair from lead 220. In this way, electrical stimulation may be delivered bilaterally, alternating between posterior and anterior regions on each side. The anterior left (30*a* and 30*b*) and posterior right (230*c* and 230*d*) bipolar pairs may be selected first, and the posterior left (30*c* and 30*d*) and anterior right (230*a* and 230*b*) bipolar pairs may be selected second in a repeated, alternating fashion to maintain tongue 40 in a protruded state continuously during an extended time period encompassing multiple respiratory cycles. In other examples, both of the anterior pairs (30*a*-30*b* and 230*a*-230*b*) may be selected simultaneously first, and both the posterior pairs (30*c*-30*d* and 230*c*-230*d*) may be selected simultaneously second, sequentially following the anterior pairs. In this way, continuous bilateral stimulation may be achieved while sequentially alternating between posterior and anterior portions to avoid or reduce fatigue.

It is to be understood that more or fewer than the four electrodes shown in the examples presented herein may be included along the distal portion of a lead used in conjunction with the OSA therapy techniques disclosed herein. A lead carrying multiple electrodes for delivering OSA therapy may include 2, 3, 5, 6 or other selected number of electrodes. When the lead includes only two electrodes, a second lead having at least one electrode may be included to provide at least two different bipolar electrode pairs for sequential stimulation of different portions of the right and/or left medial HGNs. Furthermore, while the selected electrode pairs are generally referred to herein as "bipolar pair" including one cathode and one return anode, it is recognized that three or more electrodes may be selected at a time to provide desired electrical field or stimulation vector for recruiting a desired portion of the protrusor muscles. Accordingly the cathode of a bipolar "pair" may include one or more electrodes selected simultaneously from the available electrodes and/or the anode of the bipolar "pair" may include one or more electrodes selected simultaneously from the available electrodes.

Figure 8:
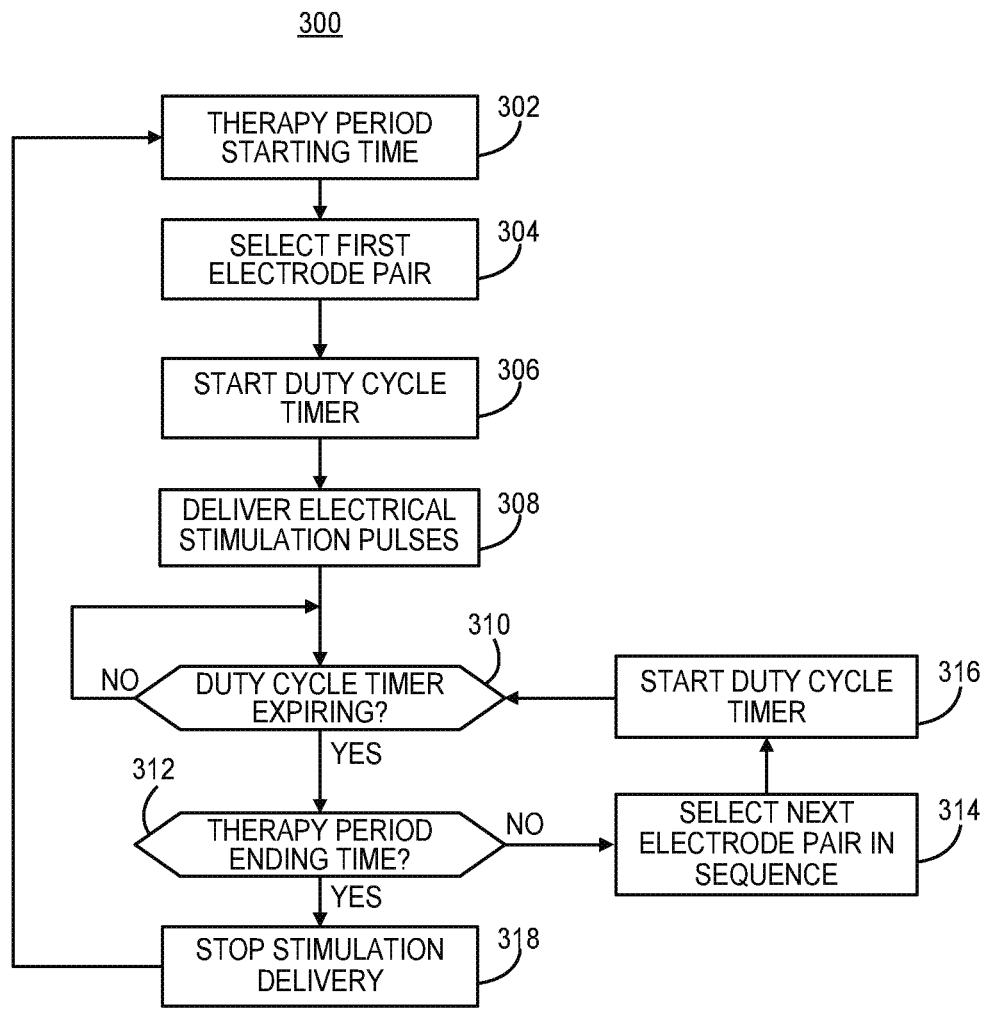
FIG. 8 is a flow chart of a method performed the system of FIG. 1 for delivering OSA therapy according to one example.

FIG. 8 is a flow chart 300 of a method performed pulse generator 12 for delivering OSA therapy according to one example. The method of flow chart 300 may be performed in conjunction with one or more leads positioned for stimulating the medial HGN as described above in conjunction with FIGS. 4-7, including at least two selectable electrode pairs. At block 302, control circuit 80 determines that a therapy delivery period starting time is reached. The therapy may be scheduled to start at a specified time of day or at every n hour interval, e.g. at 24 hour intervals. In other examples, the starting time of the therapy deliver period may be triggered based on detecting that the patient is likely to be asleep, e.g., based on signals from sensor 86 as described above such as a posture signal, patient activity signal, airway sounds or the like. In still other examples, the starting time of a therapy delivery period may be started manually by the patient using the external programmer 50, tapping on the pulse generator 12 or other means. The starting time may be delayed from the time that a manual therapy initiation signal is received, e.g., by 15 to 30 minutes, to allow time for the patient to fall asleep.

In response to determining that a therapy period start time is reached, control circuit 80 selects the first electrode pair (or combination of pairs) of a sequence of electrode pairs at block 304. The first electrode pair (or combination of two or more pairs) is selected from among the available electrodes carried by one or more leads, as described above in conjunction with FIGS. 4-8. At block 306, control circuit 80 starts a duty cycle timer for controlling the duty cycle time interval that electrical stimulation is delivered using the first selected electrode pair(s). The duty cycle time interval may be selected to be within the aerobic limit of the recruited muscle fibers in some examples. In other examples, the duty cycle time interval may extend beyond the aerobic limit but an adequate recovery time interval may be allowed before the first electrode pair(s) is/are selected again to avoid fatigue. The duty cycle timer may be set to five seconds or less in some examples.

During the duty cycle time interval, electrical stimulation pulses are delivered at block 308 (from the beginning to the end of the duty cycle time interval) to produce a fused contraction of at least a portion of the protrusor muscles to cause a sustained protruded state of the patient's tongue. The stimulation pulses may be delivered according to pulse control parameters, which may be stored in memory 82 (FIG. 3). For example, the pulse amplitude, pulse width, and pulse frequency may be selected to promote recruitment of the protrusor muscle fibers and fusion of the twitch response to each individual pulse to produce a sustained protruded state of the tongue. Examples of pulse control parameters may include pulse amplitudes between 0.1 volts and 10 volts, pulse width between 10 microseconds and 1000 microseconds, and pulse frequency between 10 Hz and 50 Hz. In other examples, pulse amplitude is between 0.5 and 8 volts, pulse width is between 40 and 500 microseconds, and pulse frequency is between 20 and 40 Hz. The pulse control parameters may be tailored to a given patient to provide a gentle protrusion of the patient's tongue that adequately opens the upper airway without causing pain or discomfort. In some examples, the electrical stimulation pulses may be ramped up in amplitude or pulse width to provide a gradual onset of the sustained protruded state.

The electrical stimulation is delivered using the first selected electrode pair(s) until the duty cycle timer expires at block 310. Upon expiration of the duty cycle timer, control circuit 80 may determine whether the therapy period ending time has been reached at block 312. The therapy period ending time may be determined based on a scheduled time interval from the starting time or a scheduled time of day. In other examples, the ending time may be determined based on signals from sensor 86 that indicate that the patient is no longer sleeping or that the OSA therapy is no longer needed. For instance, a change from a lying to upright posture may be detected, a change from a resting level of patient physical activity to a non-resting level may be detected, or other sensor signals may be used to detect that the patient is no longer asleep. In still other examples, the patient may manually signal the pulse generator 12 that OSA therapy is no longer needed, e.g., using external programmer 50.

When the therapy period ending time is detected, the electrical stimulation is terminated at block 318. The electrical stimulation may optionally be ramped down, e.g., by decreasing the pulse amplitude or pulse width over a ramp down interval to gently return the tongue to a relaxed state. Control circuit 80 may return to block 302 to wait for the next therapy period starting time. In some examples, the control circuit 80 does not need to wait until the end of a duty cycle time period at block 310 in order to detect the therapy period ending time at block 312 and terminate electrical stimulation delivery. Electrical stimulation may be terminated during a duty cycle time interval, prior to expiration of the duty cycle timer, particularly when relatively long duty cycle time intervals are utilized.

When the duty cycle timer is determined to be expiring at block 310 but the therapy period ending time has not been reached ("no" branch of block 312), the next electrode pair(s) in an electrode selection sequence is/are selected at block 314. The next electrode pair(s) may be selected to deliver stimulation that activates a different portion of the protrusor muscles than the first electrode pair(s), such as a change between left and right portions of the protrusor muscles, a change between relatively more anterior and posterior portions of the protrusor muscles, or both as generally described above in conjunction with the examples of FIGS. 4-7. While the selected electrode pairs may be referred to hereafter as singular, such as "a first selected electrode pair" and "a second electrode pair," it is recognized, as described above, the two or more electrodes may be simultaneously in one or more stimulation electrode vectors for a given duty cycle time interval.

Upon selection of the next electrode pair at block 314, control circuit 80 starts a duty cycle timer at block 316 for controlling a time interval over which electrical stimulation pulses are delivered using the next electrode pair(s). In some examples, the duty cycle time intervals of the first electrode pair and the duty cycle time interval of the second electrode pair are overlapping. Switching circuit 96 may couple the second electrode pair to the output circuit 94 prior to expiration of the first duty cycle timer. The output circuit 94 may include multiple output capacitors or channels such that the second electrode pair is coupled to a different output channel than the first electrode pair. A second duty cycle timer may be started at block 316 prior to expiration of the first duty cycle timer. Electrical stimulation pulses may be delivered using both the first electrode pair and the second electrode pair during a final segment of the first duty cycle or during overlapping portions of the first duty cycle time interval and the second duty cycle time interval. In some examples, the electrical stimulation using the second electrode pair is ramped up during the final segment of the first duty cycle or overlapping portions of the first duty cycle time period and second duty cycle time period. The electrical stimulation pulses delivered using the first electrode pair may be ramped down over the same time segment so that by the expiration of the first duty cycle, the protrusor muscles are activated by the electrical stimulation delivered using the second electrode pair in a manner that sustains the protruded state of the tongue.

In some cases, the duty cycle timer started at block 306 expires after an overlapping time segment of electrical stimulation using both the first and second electrode pairs. The same duty cycle timer may be restarted at block 316 to time out the next duty cycle time interval for electrical stimulation delivery using the next electrode pair in the sequence. In other examples, as soon as the next electrode pair in the sequence is selected and electrical stimulation via the next electrode pair is started, a second duty cycle timer may be started at block 316 to begin timing out a duty cycle time interval over which electrical stimulation is delivered using the next electrode pair. As such, control circuit 80 may include one or more duty cycle timers as needed to time out the overlapping or non-overlapping electrical stimulation time intervals in the sequence of electrode pair selections.

The duty cycles of each electrode pair in the electrode pair selection sequence may be the same or different. For example, if two electrode pairs are selected in an alternating sequence, each electrode pair may be used to deliver electrical stimulation for 50% duty cycles over the therapy period. If four different electrode pairs are selected sequentially, each electrode pair may have a 25% duty cycle. In other examples, however, the duty cycles may not be equal. For example, electrical stimulation via one electrode pair in the selection sequence may more effectively open the upper airway than electrical stimulation delivered using another electrode pair in the sequence. A longer duty cycle, e.g., 60% or 70% may be applied to the more effective electrode pair so that more effective opening of the upper airway is achieved a majority of the time. A shorter duty cycle, e.g., 30% or 40%, may be applied to the somewhat less effective electrode pair to provide sufficient metabolic recovery time to the muscle portions stimulated at the higher duty cycle while still maintaining a protruded state of the tongue and acceptable opening of the airway. In other examples, a relatively shorter duty cycle may be used for a given electrode pair selection when the muscle fibers being stimulated are more susceptible to fatigue or need to be stimulated with higher frequency or stimulation pulse energy in order to achieve an acceptable protrusion of the tongue and maintain an open airway.

This process continues of selecting sequential electrode pairs for delivering electrical stimulation over each respective duty cycle time interval until the therapy period ending time is reached at block 312. It is recognized that at least two but three, four or more electrode pairs or combinations of pairs may be selected in a repeating sequence over the entire duration of the therapy period to maintain the tongue in a protruded state independent of the timing of the respiratory cycles.

Figure 9:
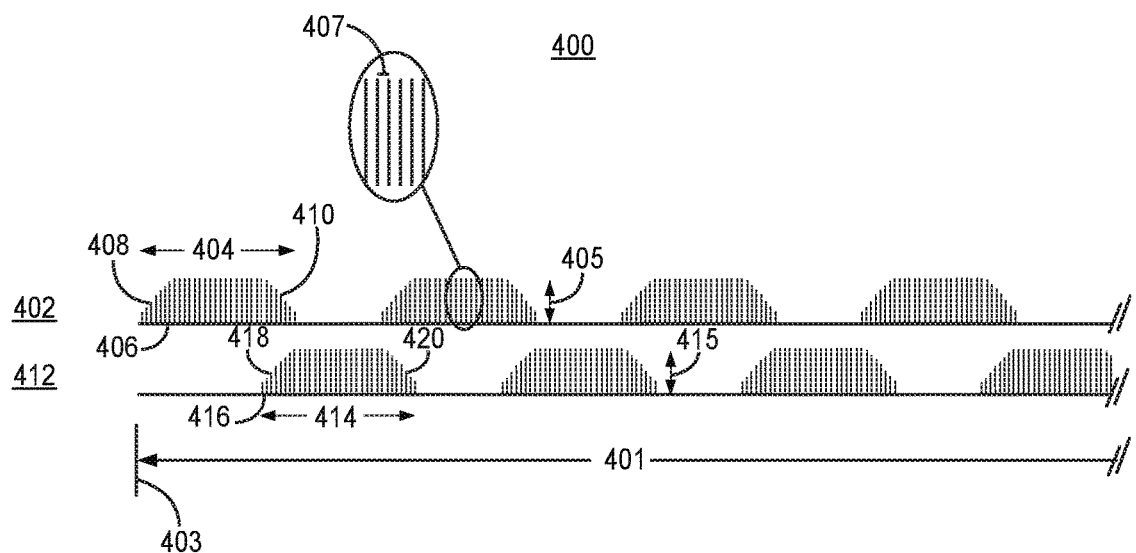
FIG. 9 timing diagram illustrating a method performed by the system of FIG. 1 for delivering selective stimulation to the protrusor muscles for promoting upper airway patency during sleep according to one example.

FIG. 9 timing diagram illustrating a method performed by pulse generator 12 for delivering selective stimulation to the protrusor muscles for promoting upper airway patency during sleep according to one example. Electrical stimulation is delivered over a therapy time period 401 having a starting time 403 and an ending time (not shown). Electrical stimulation pulses that are delivered when pulse generator sequentially selects a first bipolar electrode pair 402 and a second bipolar electrode pair 412 in an alternating, repeating manner are shown. The first and second bipolar electrode pairs 402 and 412 may correspond to any two different electrode pairs described in the examples above in conjunction with FIGS. 4-7.

A first train of electrical pulses 406 is shown starting at the onset 403 or therapy time period 401. The first train of electrical pulses 406 is delivered using bipolar electrode pair 402 for a duty cycle time interval 404. The first train of electrical pulses 406 has a pulse amplitude 405 and pulse frequency, e.g., 20 to 50 Hz, defined by the interpulse intervals 407. The first train of electrical pulses 406, also referred to as "pulse train" 406, may have a ramp on portion 408 during which the pulse amplitude is gradually increased from a starting voltage amplitude up to pulse voltage amplitude 405. In other examples, the pulse width may be gradually increased. In this way the delivered pulse energy is gradually increased to promote a gentle transition from the relaxed, non-stimulated state to the protruded state of the tongue.

The train of electrical pulses 406 may include a ramp off portion 410 during which the pulse amplitude (and/or pulse width) is decremented from the pulse voltage amplitude 405 to an ending amplitude at the expiration of the duty cycle time interval 404. In other examples, pulse train 406 may include a ramp on portion 408 and no ramp off portion 410. In this case, the last pulse of pulse train 406 delivered at the expiration of duty cycle time interval 404 may be delivered at the full pulse voltage amplitude 405. Upon expiration of the duty cycle time interval 404, electrical stimulation delivery via bipolar electrode pair 402 is terminated.

In the example shown, a second electrode pair 412 is selected when of duty cycle time interval 404 is expiring. The second electrode pair 412 may be selected such that delivery of electrical stimulation pulse train 416 starts a ramp on portion 418 that is simultaneous with the ramp of portion 410 of train 406. In other examples, the ramp on portion 418 of pulse train 416 may start at the expiration of the first duty cycle time interval 404. When pulse train 406 does not include a ramp off portion 410, the pulse train 416 may be started such that the ramp on portion 418 ends just before, just after or coincidentally with the expiration of duty cycle time interval 404. The second pulse train 416 has a duration of duty cycle time interval 414 and may end with an optional ramp off portion 420, which may overlap with the ramp on portion of the next pulse train delivered using the first electrode pair 402.

In this example, pulse trains 406 and 416 are shown to be equivalent in amplitude 405 and 415, pulse width, pulse frequency (and inter pulse interval 407), and duty cycle time interval 404 and 414. It is contemplated, however, that each of the stimulation control parameters used to control delivery of the sequential pulse trains 406 and 416 may be separately controlled and set to different values as needed to achieve a desired sustained protrusion of tongue 40 while avoiding or minimizing fatigue.

The sequential pulse trains 406 and 416 are delivered using two different electrode pairs 402 and 412 such that different portions of the protrusor muscles are recruited by the pulse trains 406 and 416 allowing one portion to rest while the other is being stimulated. However, pulse trains 404 and 406 occur in a sequential overlapping or non-overlapping manner such that electrical pulses are delivered at one or more selected frequencies for the entire duration of the therapy time period 401 to sustain the tongue in a protruded state throughout time period 401. It is to be understood that the relative down and/or forward position of the protruded tongue may shift or change as different electrode pairs are selected but the tongue remains in a protruded state throughout therapy time period 401.

At times, the pulse trains 404 and 406 may be overlapping to simultaneously recruit the left and right GG and/or GH muscles to create a relatively greater force (compared to recruitment of a single side) to pull the tongue forward to open an obstructed upper airway. In some cases, the overlapping pulse trains 404 and 406 may cause temporary fatigue of the protrusor muscles along the left or right side but the temporary fatigue may improve the therapy effectiveness to ensure an open upper airway during an apneic episode. Recovery from fatigue will occur between duty cycles and at the end of an apneic episode. Duty cycle lengths may vary between patients depending on the fatigue properties of the individual patient. Control circuit 80 may control the duty cycle on time in a manner that minimizes or avoids fatigue in a closed loop system using a signal from sensor 86, e.g., a motion sensor signal and or EMG signal correlated protrusor muscle contraction force and subsequent fatigue.

Figure 10:
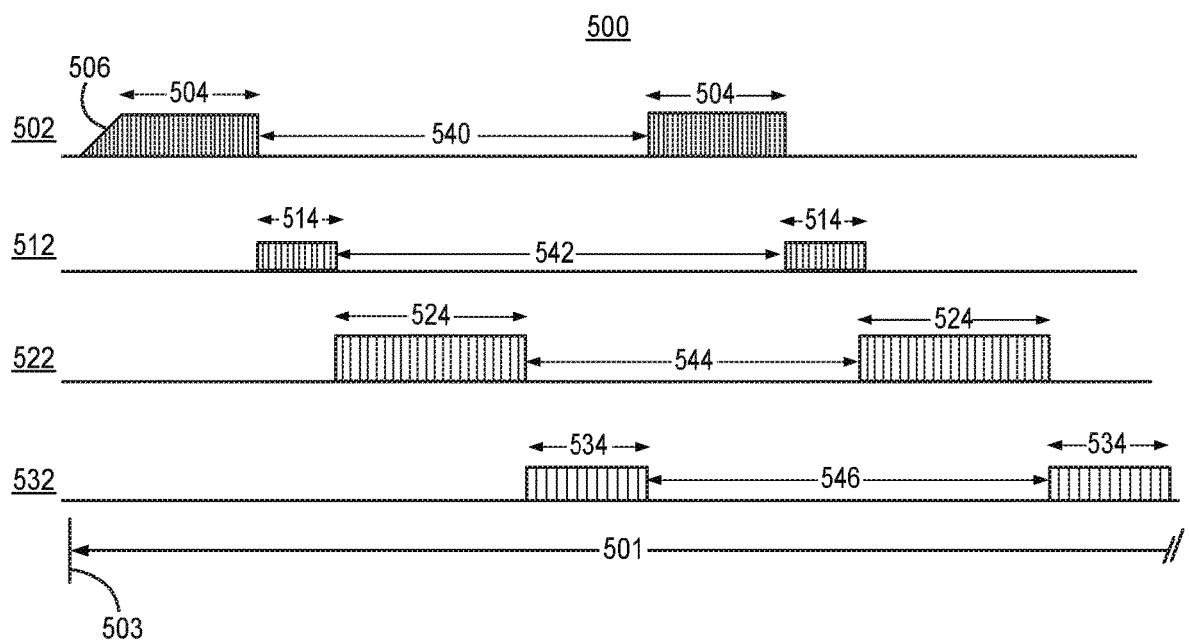
FIG. 10 is a timing diagram of a method for delivering OSA therapy by the system of FIG. 1 according to another example.

FIG. 10 is a timing diagram 500 of a method for delivering OSA therapy by pulse generator 12 according to another example. In this example, a therapy delivery time period 501 is started at 503 with a ramp on interval 506 delivered using a first bipolar electrode pair 502. The ramp on interval 506 is followed by a duty cycle time interval 504. Upon expiration of the duty cycle time interval 504, a second bipolar electrode pair 512 is selected for delivering electrical stimulation pulses for a second duty cycle time interval 514. A third duty cycle time interval 524 starts upon the expiration of the second duty cycle time interval 514, and stimulation pulses are delivered by selecting a third bipolar electrode pair 522 different than the first two pairs 502 and 512. A fourth bipolar pair 532 is selected upon expiration of the third duty cycle time interval 524 and used to deliver stimulation pulses over the fourth duty cycle time interval 534. Upon expiration of the fourth duty cycle time interval 534, the sequence is repeated beginning with duty cycle time interval 504 again.

In this example, four different bipolar pairs are selected in sequence. The four different bipolar electrode pairs may differ by at least one electrode and/or the polarity of another bipolar electrode pair. For example, when a single quadripolar lead 20 is used, the four bipolar pairs may include 30a-30b, 30b-30c, 30c-30d and 30a-30d. The portions of the protrusor muscles recruited by the four different pairs may not be mutually exclusive since the electrical fields of the four different pairs may stimulate some of the same nerve fibers. Four different portions of the protrusor muscles may be recruited, which may include overlapping portions. The relatively long recovery periods 540, 542, 544 and 546 between respective duty cycle time intervals allows each different portion of the protrusor muscles to recover before the next duty cycle. When recruited muscle portions overlap between selected electrode pairs, the bipolar electrode pairs may be selected in a sequence that avoids stimulating the overlapping recruited muscle portions consecutively. All recruited muscle portions are allowed to recover during at least a portion of each respective recovery period 540, 54, 544 and/or 546. For example, if the bipolar electrode pair 502 and the bipolar electrode pair 522 recruit overlapping portions of the protrusor muscles, the recruited portions may still recover during the second duty cycle time interval 514 and during the fourth duty cycle time interval 534.

The duration of each duty cycle time interval, 504, 514, 524 and 534, may be the same or different from each other, resulting in the same or different overall duty cycles. For example, when four bipolar electrode pairs are sequentially selected, stimulation delivery for each individual pair may be a 25% duty cycle. In other examples, a combination of different duty cycles, e.g., 30%, 10%, 40% and 20%, could be selected in order to promote sustained protrusion of the tongue with adequate airway opening while minimizing or avoiding fatigue. The selection of duty cycle may depend on the particular muscles or muscle portions being recruited and the associated response (position) of the tongue to the stimulation for a given electrode pair selection.

The stimulation control parameters used during each of the duty cycle time intervals 504, 514, 524, and 534 for delivering electrical pulses using each of the different bipolar electrode pairs 502, 512, 522 and 532 may be the same or different. As shown, a different pulse voltage amplitude and a different interpulse interval and resulting pulse train frequency may be used. The pulse amplitude, pulse width, pulse frequency, pulse shape or other pulse control parameters may be controlled according to settings selected for each bipolar electrode pair.

In the example shown, one ramp on portion 506 of the stimulation protocol is shown at the onset of the therapy delivery time period 501. Once the stimulation is ramped up to position the tongue in a protruded position, no other subsequent duty cycle time intervals 504 (other than the first one), 514, 524 and 534 may include or be proceeded by a ramp on portion. In other examples, a ramp on portion may precede each duty cycle time interval (or be included in the duty cycle time interval as shown in FIG. 9) and may overlap with the preceding duty cycle time interval. No ramp off portions are shown in the example of FIG. 10. In other examples, ramp off portions may follow or be included in each duty cycle time interval 504, 514, 524 and 534 and may overlap with the onset of the next duty cycle time interval as shown in FIG. 9. In some examples, only the last duty cycle time interval (not shown in FIG. 10) may include or be immediately followed by a ramp off portion to gently allow the tongue to return to a relaxed position at the end of the therapy delivery time period 501.

Figure 11:
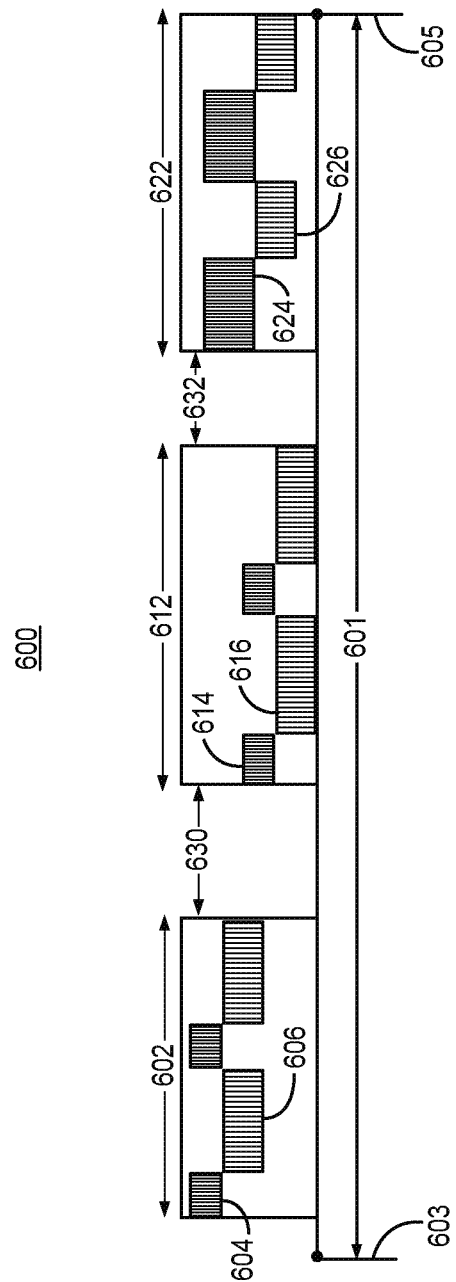
FIG. 11 is a timing diagram illustrating a period of sleep during which OSA therapy is delivered during multiple therapy delivery time periods.

FIG. 11 is a timing diagram illustrating a period of sleep 601 during which OSA therapy is delivered during multiple therapy delivery time periods 602, 612 and 622. In some examples, the one long therapy delivery time period may extend over the time that the patient is asleep at night such that stimulation pulses are delivered continuously over the entire therapy delivery time period to continuously deliver OSA therapy throughout the time the patient is asleep. Even though the stimulation pulses may vary in frequency, amplitude, and delivery electrode pair during the sequential duty cycle time intervals as shown in FIG. 10, the stimulation pulses are delivered without gaps or breaks in time. In FIG. 11, multiple therapy delivery time periods 602, 612 and 622 may span the time that the patient is asleep 601.

During each therapy delivery time period 602, 612, and 622, two or more different bipolar electrode pairs may be selected and used to deliver electrical stimulation pulses according to two different sequential duty cycle time intervals 604 and 606, 614 and 616, and 624 and 626, respectively. The electrode pairs and other stimulation control parameters may be the same or uniquely specified for each of the different therapy delivery time periods 602, 612 and 622. By using different combinations of sequentially selected electrode pairs, for example, a longer recovery time may be provided for the muscle portions recruited during one therapy delivery time period and not another therapy delivery time period.

The therapy delivery time periods 602, 612 and 622 may immediately follow each other such that continuous stimulation is delivered over the sleep period 602. In the example shown, a delay 630 is shown between therapy delivery time periods 602 and 612 and another delay 632 is shown between therapy delivery time periods 612 and 622. While prevention of airway obstruction may be desired throughout sleep period 603, delays 630 and/or 632 may be provided between therapy delivery time periods 602, 612 and 622 to allow for metabolic recovery in some examples and avoid fatigue. The delays 630 and 632 may be relatively short, e.g., one to five minutes with therapy delivery periods 602, 612, and 622 lasting several minutes or even hours. In some examples, a sequence of therapy delivery time period 602, 612 and 622 may be repeated sequentially throughout sleep period 603 until the end of sleep 605 is detected or the therapy is manually terminated.

Figure 12:
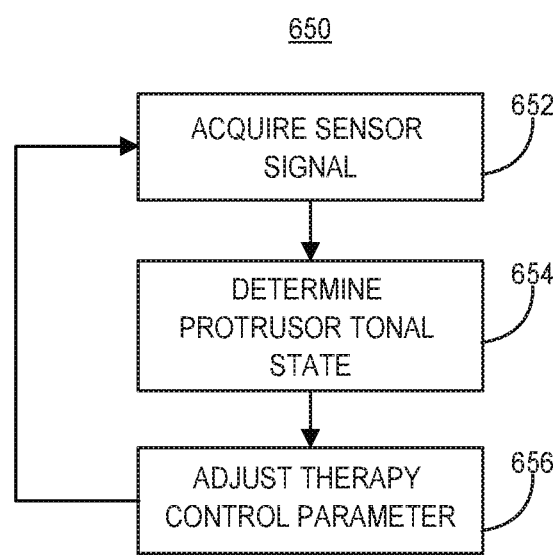
FIG. 12 is a flow chart of a method for providing OSA therapy according to one example.

FIG. 12 is a flow chart 650 of a method for delivering OSA therapy according to one example. At block 652, a signal from sensor 86 is received by control circuit 80. The signal may be a motion signal, EMG signal or other sensor signal that is produced by sensor 86 and is correlated to a tonal state of the protrusor muscle tissue. At block 654, control circuit 80 determines a tonal state of the protrusor muscle tissue based on the sensor signal. The tonal state may be a low tonal state indicative of sleep and/or presence of airway obstruction. The tonal state may be fatigue due to stimulation. In other examples, the tonal state may be a state of activation that is correlated to the degree of protrusion of the patients tongue due to force generated by the stimulated protrusor muscles. The tonal state may be determined at block 654 may be based on a relative change in amplitude, area or other analysis of the sensor signal.

At block 656, the therapy delivery circuit 84 adjusts a therapy control parameter in response to the determination of the tonal state of the protrusor muscle tissue. For example, in response to a low tonal state, therapy delivery circuit 84 may enable or turn on OSA therapy delivery and/or increase a pulse amplitude, width and/or frequency of pulse trains. In response to a change in the tonal state indicative of fatigue, therapy delivery circuit 84 may adjust the duty cycle of a stimulation electrode vector, switch to a different stimulation electrode vector pair and/or change a pattern of duty cycles delivered across multiple stimulation electrode pairs. Fatigue may be detected based on a decrease in amplitude, frequency or other feature of the sensor signal.

In some instances, a high tonal state may indicate overstimulation or excessive protrusion of the tongue which could pose a risk of fatigue, patient discomfort or sleep disturbance. In this case, therapy delivery circuit 84 may decrease the pulse amplitude and/or width, pulse frequency, overlap of duty cycles, and/or switch the stimulation electrode vector selection. Sensor signal monitoring of the tonal state of the protrusor muscle tissue may be performed by control circuit 80 to provide closed loop control of therapy delivered by therapy delivery circuit 84.

Figure 13:
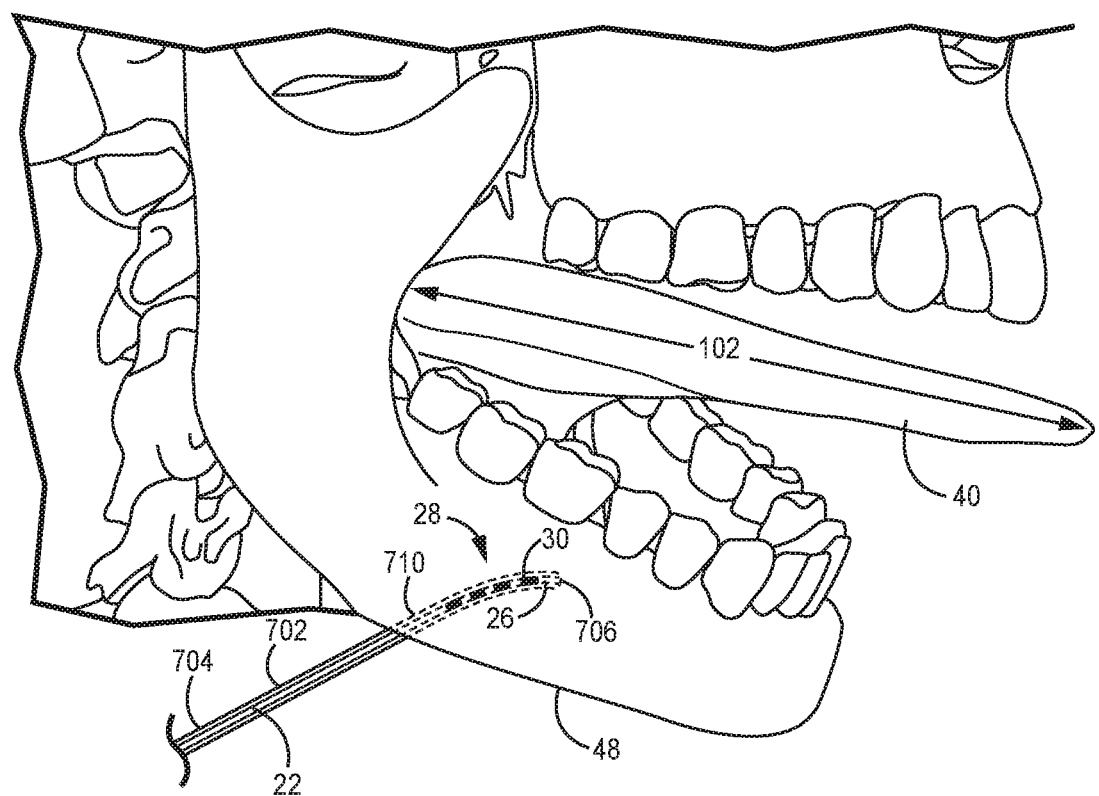
FIG. 13 is a conceptual diagram of an implant method for positioning the distal portion 28 of the lead of FIG. 2 along a target region for electrical stimulation delivery.

FIG. 13 is a conceptual diagram of an implant method for positioning the distal portion 28 of lead 20 along a target region for electrical stimulation delivery. A hollow needle 702 having an open lumen 704 and tissue piercing distal tip 706 may be advanced percutaneously in a generally superior and anterior direction from an approach beneath the mandible 48, in order to begin the process of creating an elongated aperture through the soft tissues below the floor of the oral cavity. The hollow needle 702 may be advanced to form an aperture that is approximately perpendicular, parallel or oblique to the midline of tongue 40 and a medial plane of the mandible. A skin puncture may be created beneath the mandible, along the inferior surface of the chin, however other approaches may also be suitable and may be patient specific, e.g., downward into the floor of the oral cavity from an approach within the oral cavity.

The needle 702 may be advanced from a relatively posterior puncture site toward an anterior direction to create a track along or through the GG and/or GH muscles. In other examples, the needle 702 may be advanced in a medial-lateral direction for a more oblique or perpendicular position relative to the midline 102 of tongue 40, crossing a medial plane of the jaw. The distal end 26 of the lead 20 is advanced through the lumen 704 of the needle 702. The lead 20 is advanced through lumen 704 until electrodes 30 are positioned along or in one or both of the left and right target regions of the medial HGN as shown in any of the examples of FIGS. 4-7. Needle 702 is gradually removed by pulling the needle 702 in a reverse or proximal direction. As the needle 702 is removed, the lead 20 may be slowly moved further into the target region in some examples. The needle 702 is then fully removed from the patient, leaving the distal portion 28 of lead 20 positioned for therapy delivery. In particular, the electrodes 30 remain in close proximity of the left and/or right medial HGN and branches thereof to stimulate the nerves for recruitment of the protrusor muscles of the tongue 40. In other examples, the protrusor muscle fibers are stimulated directly.

In some examples, needle 702 includes a curved portion 710 near the distal tissue-piercing tip 26. The curved portion 710 may be provided to guide advancement along a path that enters the soft tissues below the oral cavity and advances anteriorly (e.g., as shown in FIGS. 5-7) or from a relatively lateral approach that continues medial-laterally toward midline 102 (for a deployment as shown in FIG. 4, for example). A curved portion 710 may enable placement of distal portion 28 at an orientation relative to the left and/or right target regions of the medial HGN that may not be possible with a straight needle. The final implant location of distal portion 28 may be intramuscularly within the GG and/or GH muscles and/or within other soft tissue proximate the medial HGN branches, below the floor of the oral cavity and without penetrating the oral cavity.

Figure 14:
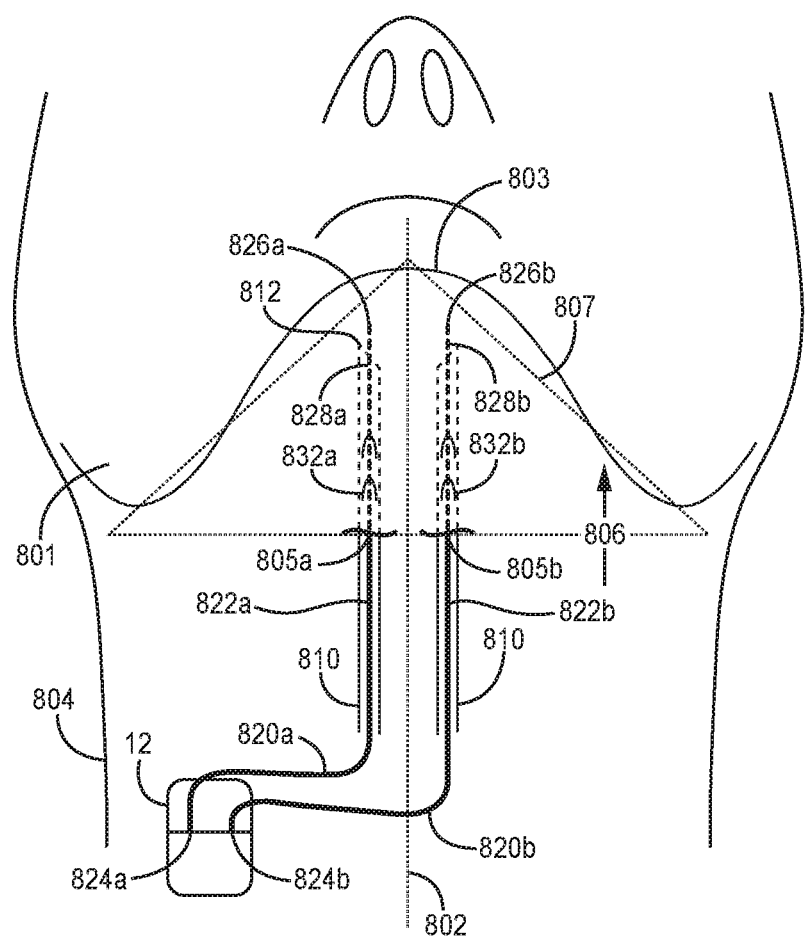
FIG. 14 is a conceptual diagram of a method for providing an OSA therapy according to another example.
Figure 15:
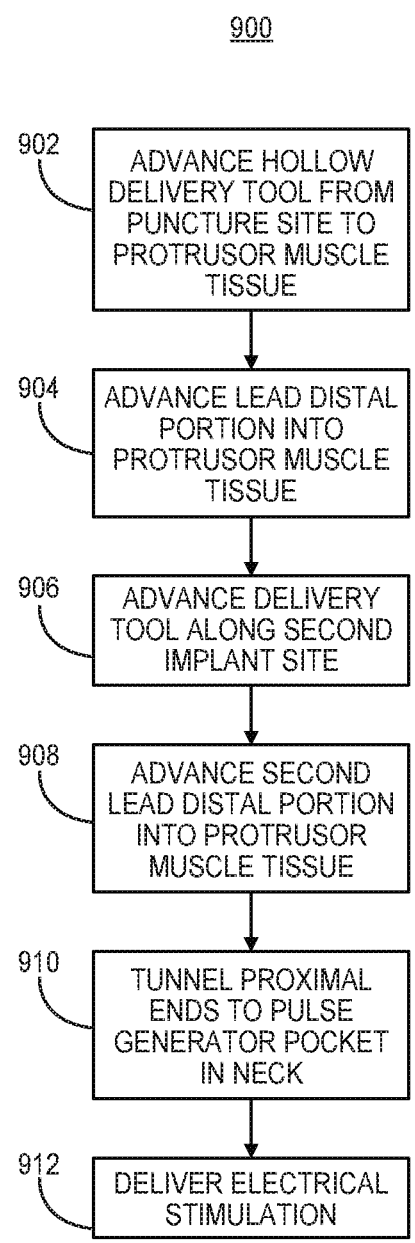
FIG. 15 is a flow chart of a method for providing an OSA therapy according to another example.

FIG. 14 is a conceptual diagram of a method for providing an OSA therapy, and FIG. 15 is a flow chart of the method of FIG. 14 according to another example. With reference to both FIGS. 14 and 15, at block 902 a hollow delivery tool 810, which may be a hollow needle with a sharpened or beveled distal tip 812, may be inserted percutaneously at an insertion or puncture site 805a and advanced adjacent to a medial plane 802 of the patient's neck 804 and mandible 801, which may correspond to the midline of the patient's tongue (e.g., see FIG. 7). The insertion site 805a may be relatively posterior along the anterior triangle 807 of the neck beneath the body of the mandible 801, e.g., corresponding to the submandibular triangle and submental triangle.

The delivery tool 810 is advanced superiorly without puncturing into the oral cavity then in a generally posterior to anterior direction 806. The delivery tool 810 may be advanced generally parallel to the medial plane 802, laterally offset from the medial plane 802, toward the target region of the medial HGN (e.g., see regions 106L and 106R of FIG. 7). When the distal tip 812 of the delivery tool 810 has reached a desired site within or along the protrusor muscles, the lead distal portion 828a, carrying multiple electrodes as shown in FIG. 2, is advanced through the hollow lumen of the delivery tool 810 (block 904) to position the electrodes along or in the protrusor muscle tissue along one side of the medial plane 802. The lead 820a may include a fixation member 832a including multiple tines or other structures that may collapse along lead body 822a when constrained within delivery tool 810 and expand to a normal position upon release from delivery tool 810 to engage with surrounding tissue to prevent shifting of distal portion 828a.

In the example shown, a second lead 820b is advanced percutaneously to position the second distal portion 828b, carrying at least one electrode, in or along protrusor muscle tissue on the opposite side of medial plane 802 from the first distal portion 828a of the first lead 820a. As such, at block 906, a hollow delivery tool 810 may be advanced from a second insertion site 805b. The second insertion site 805b may be relatively posterior along the anterior triangle 807 of the patient's neck 804 as described above with regard to insertion site 805a, but insertion site 805b is laterally offset from medial plane 802 on a side opposite the first insertion site 805a. The distal end 826b of second lead 820b is advanced (at block 908) through the delivery tool 810 to position the second distal portion 828b along a target region for stimulation of the medial HGN along the second side opposite the medial plane 802 from the first distal portion 828a. The two lead distal portions 828a and 828b may extend approximately parallel to each other and adjacent to the medial plane 802. The fixation member 830b along the second lead body 822b engages with surrounding tissue upon extraction of delivery tool 810 to prevent shifting or dislodgment of distal portion 828b.

The proximal ends 824a and 824b of each respective lead 820a and 820b may be tunneled from the respective insertion sites 805a and 805b to an implant pocket along the patient's neck 804 (block 910), where each of the proximal ends 824a and 824b are coupled to the pulse generator 12. Each of the lead bodies 822a and 822b may have an overall length from respective distal end 826a to proximal end 824a and distal end 826b to proximal end 824b that extends a maximum distance along the patient's neck 804 to be coupled to pulse generator 12 implanted along the neck, e.g., below mandible 801 and above the patient's collar bone. For example, the overall length of leads 820a and 820b may be approximately 10 cm to approximately 25 cm. The overall length of leads 820a and 820b may vary in different examples in order to accommodate different patient sizes and different implant locations in the neck, e.g., a relatively short person with the pulse generator implanted high in the neck versus a relatively tall person with the pulse generator implanted relatively low in the neck, nearer to the collar bone than the mandible 801. An overall maximum length of leads 820a and 820b may be up to 25 cm as an example.

Electrical stimulation pulses are delivered (block 912) using the electrodes carried by the lead distal portions 828a and 828b to activate the protrusor muscles to sustain a protruded state of the patient's tongue throughout a therapy delivery period. Two or more bipolar electrode pairs may be selected sequentially from the available electrodes carried by the two leads 820a and 820b to deliver the electrical stimulation pulses according to two or more duty cycles to activate different portions of the protrusor muscles in a sequential manner to avoid or reduce fatigue while sustaining the protruded state over an extended therapy delivery period. In some examples, each bipolar pair is selected to include electrodes only from one of the leads 820*a* or 820*b* but not both such that portions of the left and right sides of the protrusor muscles are sequentially activated by respective left and right bipolar electrode pairs. In other examples, a bipolar pair may include one electrode from one lead 820*a* and one electrode from the other lead 820*b* so that sequential stimulation may include bilateral portions of the protrusor muscles, e.g., an anterior bilateral portion and a posterior bilateral portion. The electrical stimulation duty cycles and pulse trains delivered at block 912 using the two leads 820*a* and 820*b* positioned as generally shown in FIG. 14 may correspond to any of the examples given above, e.g., in conjunction with FIGS. 9-11.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single module or unit for purposes of clarity, it should be understood that the techniques of this disclosure may be performed by a combination of units or modules associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, an implantable medical device system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A method, comprising:
    advancing a hollow delivery tool percutaneously into protrusor muscle tissue below an oral cavity of a patient without penetrating into the oral cavity;
    advancing a first distal portion of a first elongated lead body of a first medical electrical lead percutaneously into the protrusor muscle tissue below the oral cavity via the delivery tool without penetrating into the oral cavity to position a first plurality of electrodes carried by the first distal portion within the protrusor muscle tissue, wherein the first plurality of electrodes are configured to be implanted proximate, and without attaching, to a nerve of the protrusor muscle tissue and proximate to a motor point of at least one protrusor muscle of the protrusor muscle tissue; and
    delivering electrical stimulation pulses via the first plurality of electrodes to activate the protrusor muscle tissue to sustain a protruded state of a tongue of a patient throughout a therapy delivery time period that comprises a plurality of respiration cycles, wherein delivering the electrical stimulation pulses comprises delivering the electrical stimulation pulses to the motor point of the at least one protrusor muscle of the protrusor muscle tissue.

2. The method of claim 1, further comprising sequentially selecting a plurality of different bipolar electrode pairs from the first plurality of electrodes during the therapy delivery time period.

3. The method of claim 2, further comprising:
    advancing the first distal portion across a medial plane of the protrusor muscle tissue to position at least a first bipolar electrode pair of the first plurality of electrodes for stimulating a left portion of the protrusor muscle tissue and at least a second bipolar pair of the first plurality of electrodes for stimulating a right portion of the protrusor muscle tissue;
    sequentially selecting the first and second bipolar electrode for sequentially activating a left protrusor muscle and a right protrusor muscle for sustaining the protruded state of the tongue throughout the therapy delivery time period.

4. The method of claim 3, wherein advancing the first distal portion across the medial plane comprises advancing the first distal portion obliquely across the medial plane.

5. The method of claim 1, further comprising:
    advancing the first distal portion along a medial plane of the protrusor muscle to position at least a first bipolar electrode pair of the first plurality of electrodes for stimulating a posterior portion of the protrusor muscle tissue and at least a second bipolar pair of the first plurality of electrodes for stimulating an anterior portion of the protrusor muscle tissue;
    sequentially selecting the first and second bipolar electrode pairs to activate muscle tissue of an anterior portion of protrusor muscles of the tongue and a second pair of the plurality of electrodes different than the first pair for activating muscle tissue of a posterior portion of protrusor muscles of the tongue.

6. The method of claim 1, wherein delivering the electrical stimulation pulses comprises continuously delivering the electrical stimulation pulses from a starting time of the therapy delivery time period to an ending time of the therapy delivery time period by:
    selecting a first bipolar pair from the first plurality of electrodes;
    delivering a first portion of the electrical stimulation pulses via the first bipolar electrode pair for a first duty cycle of the therapy delivery time period;
    selecting a second bipolar pair from the first plurality of electrodes;
    delivering a second portion of the electrical stimulation pulses via the second bipolar electrode pair for a second duty cycle of the therapy delivery time period.

7. The method of claim 6, further comprising delivering the first portion of the electrical stimulation pulses for the first duty cycle and delivering the second portion of the electrical stimulation pulses the second duty cycle independent of inspiratory and expiratory phases of the plurality of respiration cycles.

8. The method of claim 1, further comprising:
sensing a sensor signal that is correlated to a protrusor muscle tone during the therapy delivery time period;
determining a state of the protrusor muscle tone based on the sensor signal; and
adjusting the electrical stimulation pulses during the therapy delivery time period based on the determined state of the protrusor muscle tone.

9. The method of claim 1, further comprising advancing the hollow delivery tool percutaneously at a submandibular insertion site and further into the protrusor muscle tissue.

10. The method of claim 1, wherein advancing the hollow delivery tool comprises advancing the hollow delivery tool percutaneously from a submandibular insertion site and along a posterior to anterior pathway into the protrusor muscle tissue; and
advancing the first distal portion along the posterior to anterior pathway into the protrusor muscle tissue.

11. The method of claim 1, further comprising:
advancing the first distal portion into the protrusor muscle tissue laterally adjacent to a medial plane of the protrusor muscle tissue to position the first plurality of electrodes along a first side of the protrusor muscle tissue;
advancing a second distal portion of a second medical electrical lead percutaneously into the protrusor muscle tissue below the oral cavity and laterally adjacent to the medial plane of the protrusor muscle tissue on a second side opposite the first side of the protrusor muscle tissue to position a second plurality of electrodes carried by the second distal portion along the second side of the protrusor muscle tissue; and
delivering the electrical stimulation pulses via the first plurality of electrodes and the second plurality of electrodes to activate the protrusor muscle tissue to sustain the protruded state of the patient tongue throughout the therapy delivery time period.

12. The method of claim 11, further comprising delivering the electrical stimulation pulses by sequentially selecting from the first plurality of electrodes and the second plurality of electrodes at least a first bipolar electrode pair for a first duty cycle and a second bipolar electrode pair for a second duty cycle to sustain the protruded state of the patient's tongue throughout the therapy delivery time period.

13. The method of claim 12, further comprising one of:
selecting the first bipolar pair from only the first plurality of electrodes and selecting the second bipolar pair from only the second plurality of electrodes; or
selecting the first bipolar pair by selecting at least one of the first plurality of electrodes paired with at least one of the second plurality of electrodes.

14. The method of claim 1, further comprising:
tunneling a proximal end of the first medical electrical lead to a subcutaneous pocket along a neck of the patient;
coupling the proximal end to a pulse generator implanted in the subcutaneous pocket along the neck; and
generating the electrical stimulation pulses by the pulse generator.

15. A medical device system, comprising:
a first medical electrical lead comprising:
a first elongated lead body extending from a first proximal end to a first distal end with a first distal portion proximate the first distal end, the first distal portion configured for percutaneous advancement via a hollow delivery tool within protrusor muscle tissue below an oral cavity without penetrating into the oral cavity;
a first plurality of electrodes spaced apart along the first distal portion for implantation within the protrusor muscle tissue below the oral cavity, wherein the first plurality of electrodes are configured to be implanted proximate, and without attaching, to a nerve of the protrusor muscle tissue and proximate to a motor point of at least one protrusor muscle of the protrusor muscle tissue; and
a pulse generator configured to receive the first proximal end and deliver electrical stimulation pulses to activate the protrusor muscle tissue via the first plurality of electrodes to sustain a protruded state of a tongue of a patient throughout a therapy delivery time period, and wherein to deliver electrical stimulation pulses, the pulse generator is configured to deliver the electrical stimulation pulses to the motor point of the at least one protrusor muscle of the protrusor muscle tissue.

16. The system of claim 15, wherein the pulse generator is configured to sequentially select at least a first bipolar pair and a second bipolar pair from the first plurality of electrodes during the therapy delivery time period to sequentially activate at least a first portion of the protrusor muscle tissue and a second portion of the protrusor muscle tissue, respectively, to sustain the protruded state of the tongue throughout the therapy delivery time period.

17. The system of claim 15, wherein the pulse generator is configured to continuously deliver the electrical stimulation pulses independent of inspiratory and expiratory phases of the plurality of respiration cycles from a starting time of the therapy delivery time period to an ending time of the therapy delivery time period by:
selecting a first bipolar pair from the plurality of electrodes;
delivering a first portion of the electrical stimulation pulses via the first bipolar electrode pair for a first duty cycle of the therapy delivery time period;
selecting a second bipolar pair from the plurality of electrodes;
delivering a second portion of the electrical stimulation pulses via the second bipolar electrode pair for a second duty cycle of the therapy delivery time period.

18. The system of claim 15, further comprising a sensor configured to produce a sensor signal correlated to a protrusor muscle tone,
wherein the pulse generator is configured to:
determine a state of the protrusor muscle tone based on the sensor signal; and
adjust the electrical stimulation pulses during the therapy delivery time period based on the determined state of the protrusor muscle tone.

19. The system of claim 15, further comprising a second medical electrical lead comprising:
a second elongated lead body extending from a second proximal end to a second distal end with a second distal portion proximate the second distal end, and
a second plurality of electrodes spaced apart along the second distal portion, the second distal portion configured for percutaneous advancement via a hollow delivery tool within the protrusor muscle tissue below the oral cavity without penetrating into the oral cavity and laterally adjacent to a medial plane of the protrusor muscle tissue on a side opposite the first distal portion to position the second plurality of electrodes carried by the second distal portion along the protrusor muscle tissue on an opposite side of the medial plane than the first plurality of electrodes, wherein the pulse generator is further configured to receive the second proximal end and deliver the electrical stimulation pulses by sequentially selecting from the first plurality of electrodes and the second plurality of electrodes at least a first bipolar electrode pair for a first duty cycle and a second bipolar electrode pair for a second duty cycle to sustain the protruded state of the patient's tongue throughout the therapy delivery time period.

20. The system of claim 15 wherein the first elongated lead body has a length that extends a maximum distance from the distal portion to the pulse generator when the pulse generator is implanted along a neck of the patient.

* * * * *